(12) United States Patent
Merzliakov et al.

(10) Patent No.: US 6,497,509 B2
(45) Date of Patent: Dec. 24, 2002

(54) METHOD FOR MEASURING ABSOLUTE VALUE OF THERMAL CONDUCTIVITY

(75) Inventors: Mikhail Merzliakov, Rostock (DE); Christoph Schick, Sanitz (DE)

(73) Assignee: PerkinElmer Instruments LLC, Shelton, CT (US)

(*) Notice: Subject to any disclaimer, the term of this patent is extended or adjusted under 35 U.S.C. 154(b) by 4 days.

(21) Appl. No.: 09/877,390

(22) Filed: Jun. 8, 2001

(65) Prior Publication Data

US 2002/0041619 A1 Apr. 11, 2002

Related U.S. Application Data

(60) Provisional application No. 60/210,256, filed on Jun. 8, 2000.

(51) Int. Cl.[7] .............................................. G01N 25/20
(52) U.S. Cl. .............................. 374/44; 374/10; 374/33
(58) Field of Search .............................. 374/10, 33, 44, 374/11, 31, 32, 43

(56) References Cited

U.S. PATENT DOCUMENTS

| 5,099,441 | A | * | 3/1992 | Mazzio ........................ 364/557 |
| 5,224,775 | A | | 7/1993 | Reading et al. |
| 5,335,993 | A | | 8/1994 | Marcus et al. |
| 5,346,306 | A | | 9/1994 | Reading |
| 5,439,291 | A | | 8/1995 | Reading |
| 5,599,104 | A | | 2/1997 | Nakamura et al. |
| 5,688,049 | A | | 11/1997 | Govorkov |
| 5,711,604 | A | | 1/1998 | Nakamura |
| 5,842,788 | A | | 12/1998 | Danley et al. |

FOREIGN PATENT DOCUMENTS

| JP | 63081253 A | * | 4/1988 | .......... G01N/25/20 |
| JP | 02027244 A | * | 1/1990 | .......... G01N/25/18 |
| JP | 04274748 A | * | 9/1992 | .......... G01N/25/20 |

OTHER PUBLICATIONS

P. G. Knibbe, An Accurate instrument for fast thermal–conductivity and thermal–diffusivity measurements at elevated temperatures and pressures, *J. Phys., E: Sci. Instrum.*, vol. 20, pp. 1205–1211 (1987).
D. G. Cahill and R. O. Pohl, Thermal Conductivity of amorphous solids above the plateau, *Phys. Rev. B.* vol. 35, p. 4067 (1987).
J. H. Flynn and D. M. Levin, A Method For The Determination of Thermal Conductivity of Sheet Materials By Differential Scanning Calorimetry, *Thermochimica Acta*, vol. 126, pp. 93–100 (1988).
T. Hashimoto, Y. Matsui, A. Hagiwara and A. Miyamoto; *Termochimica Acta* vol. 163, pp. 317–324 (1990).

(List continued on next page.)

Primary Examiner—Christopher W. Fulton
Assistant Examiner—Lydia M. De jesús
(74) Attorney, Agent, or Firm—St.Onge Steward Johnston & Reens LLC

(57) ABSTRACT

A method of measuring the absolute value of thermal conductivity of low thermal conducting solid materials is disclosed. Thermal conductivity and heat capacity of the sample are determined simultaneously in a single measurement with the prerequisite that these values are frequency independent. This method is realized on power-compensated differential scanning calorimeters without any modification in the measuring system. DSC is calibrated in a standard way for temperature and heat flow. The method uses temperature-time profiles consisting of one fast temperature jump of 0.5 to 2 K and an isotherm. The measuring time for each temperature is less than 1 min. As input parameters only sample thickness and contact area with the DSC furnace (or sample diameter if the sample is disk shaped) are needed together with sample mass. In addition to the sample thermal conductivity and heat capacity the effective thermal contact between sample and DSC furnace is determined.

22 Claims, 13 Drawing Sheets

OTHER PUBLICATIONS

S.M. Marcus and R.L. Blaine, Thermal Conductivity of Polymers, glasses and ceramics by modulated DSC, *Thermochimica Acta*, vol. 243, pp. 231–239 (1994).

S.L. Simon and G.B. McKenna, Measurement of Thermal Conductivity Using TMDSC: Solution to the Heat Flow Problem, *J. Reinforced Plastics Composites*, vol. 18, pp. 559–571 (1999).

Merzlyakov and C. Schick, Complex heat capacity measurements by TMDSC. Part 2. Algorithm for amplitude and phase angle correction, *Thermochimica Acta*, vol. 330, p. 65 (1999).

D. G. Cahill, Thermal Conductivity Measurement From 30 to 750 K: The 3 $\omega$Method, *Rev. Sci. Instrum.* vol. 61(2), pp. 802–808 (1990).

\* cited by examiner

METHOD FOR MEASURING ABSOLUTE VALUE OF THERMAL CONDUCTIVITY

This application claims the benefit of provisional application Ser. No. 60/210,256, filed on Jun. 8, 2000, which is expressly incorporated by reference herein.

FIELD OF THE INVENTION

The present invention relates to a method of using Differential Scanning Calorimetry ("DSC") to measure the thermal conductivity of materials.

BACKGROUND OF THE INVENTION

Thermal conductivity characterizes the ability of a material to conduct heat. Traditional methods for measuring the thermal conductivity of materials comprise imposing a temperature gradient upon a material of known geometry, and measuring the heat flow through the material. The heat flow is measured by, for example, measuring the temperature drop across a sheet of material having a known thermal conductivity. Traditional methods of measuring thermal conductivity are limited in that they assume that thermal contact of a sample is highly reproducible and determinable from a calibration measurement. The present invention overcomes this limitation by using a simultaneous thermal contact measurement. No method has been heretofore proposed to determine the actual thermal contact and the thermal conductivity simultaneously from a single measurement of a heat capacity spectrum.

Thermal conductivity data are in great demand by industry, for use in polymer injection molding, in encapsulation of electronic devices and, in general, in modeling of different processes. Nowadays commercial techniques often measure thermal diffusivity or effusivity and calculate thermal conductivity using heat capacity values, measured separately.

DSC is a commercially available and widely used technique to measure heat capacity of samples of milligram size in a wide temperature range. Therefore it would be opportune to add to DSC instruments a feature to measure thermal conductivity of typical DSC samples.

Prior art of interest includes P. G. Knibbe, J. Phys. E: Sci. Instrum., vol. 20, pp. 1205–1211 (1987) which describes a "hot wire" technique for measuring the thermal conductivity of a material. This technique uses a temperature-sensitive resistor wire embedded in a sample of the material. The resistor wire serves the dual function of supplying heat to the specimen, and measuring the temperature change at the wire. This rate of change is related to the thermal conductivity of the sample of the material.

D. G. Cahill and R. O. Pohl, Phys. Rev. B. vol. 35, p. 4067 (1987), and D. G. Cahill, Rev. Sci. Instrum. vol. 61(2), pp. 802–808 (1990), describe a "$3\omega$" technique for measuring thermal conductivity. This technique uses a temperature sensitive resistive metal film evaporated as a narrow line onto the surface of the sample to simultaneously heat the sample and detect the flow of heat away from the metal line. A current at angular frequency $\omega$ heats the metal line at a frequency of $2\omega$. Because the resistance of a metal increases with increasing temperature, and this temperature is modulated by the sample thermal conductivity, this produces a small oscillation in the resistance of the metal line, resulting in a voltage across the resistor at a frequency of $3\omega$. The thermal conductivity of the sample is then calculated from the amplitude of the $3\omega$ voltage oscillations.

J. H. Flynn and D. M. Levin, Thermochimica Acta, vol. 126, pp. 93–100 (1988), describes a thermal conductivity measurement method, suitable for measuring the thermal conductivity of sheet materials, based upon first-order transitions in a sensor material. A film of the sensor material is placed on a surface of the sheet material. The thermal conductivity measurement is made at the temperature at which the sensor material undergoes a first order transition. For example, if indium is used as the sensor material, the measurement is made at the melting point of indium, i.e., at the temperature at which indium undergoes a first order transition. The flow of heat into the sensor material must match the transition enthalpy. The thermal conductivity of the sheet material is obtained by comparing the data obtained with only the sensor material in the heater of a differential scanning calorimeter, to the data obtained with the sensor material on top of the sheet material in the differential scanning calorimeter.

T. Hashimoto, Y. Matsui, A. Hagiwara and A. Miyamoto; Termochimica Acta vol. 163, pp. 317–324 (1990), describes a method to obtain thermal diffusivity by an AC calorimetric method. The AC current is passed through the heater; the periodical heat flow generates and diffuses to the rear surface of the sample. The variation of the temperature at the rear surface was detected. A sputtered gold layer on both surfaces was used as the heater and the sensor of temperature variation. The thermal diffusivity of four polymers were measured over the temperature range 20–200° C.

S. M. Marcus and R. L. Blaine, Thermochimica Acta, vol. 243, pp. 231–239 (1994) (herein incorporated by reference), describes a thermal conductivity measurement method where thermal conductivity is measured without modification of the commercially available DSC cell. A calculation of thermal conductivity is determined from a ratio of apparent and true heat capacities measured from a thick (about 3 mm) and a thin (about 0.5 mm) sample, respectively, in temperature-modulated mode. An additional calibration step takes heat losses through the purge gas surrounding into account. This method is based on the assumption that the face of the specimen at the heat source follows the applied temperature modulation, which means no thermal resistance between the sample and the furnace.

S. L. Simon and G. B. McKenna, J. Reinforced Plastics Composites, vol. 18, pp. 559–571 (1999) (herein incorporated by reference), describes two problems in the aforesaid method of Marcus and Blaine. First, the equation relating the apparent heat capacity to the thermal conductivity is limited in range due to an approximation made in their derivation. Second, a thermal resistance between the sample and the furnace can have significant effect on the measured apparent heat capacity. This reference also teaches that when calculating a value for thermal conductivity it is necessary to know the heat transfer coefficient, for without it, an accurate value cannot be obtained.

S. L. Simon and G. B. McKenna, J. Reinforced Plastics Composites, vol. 18, pp. 559–571 (1999), as well as U.S. Pat. No. 5,335,993 to Marcus et al. (herein incorporated by reference), additionally describe a method of determining thermal conductivity by obtaining the value from a single run at several frequencies, i.e. it is not necessary to measure two samples. In U.S. Pat. No. 5,335,993 the method described therein has insufficient sensitivity, in part; because it measures the conductivity of massive bodies brought into thermal contact with thin film wafers and does not fully eliminate interface thermal resistance. The basic problem with this patent as well as S. L. Simon and G. B. McKenna, J. Reinforced Plastics Composites, vol. 18, pp. 559–571 (1999), is that the actual thermal contact between sample and oven is not considered in the calculation of thermal conductivity. Theses references teach that thermal contact is considered to be highly reproducible and determined from the calibration measurement.

U.S. Pat. No. 5,244,775 to Reading et al. and U.S. Pat. No. 5,439,291 to Reading utilize frequency measurement resulting from the application of heat to determine phase transition of materials.

U.S. Pat. No. 5,439,291 to Reading (herein incorporated by reference) describes a technique for determining physical properties of a sample using thermal modulation techniques. Two identical samples are used, with one experiencing a linear temperature ramp and the other experiencing the same ramp with a temperature oscillation imposed. A chopped light source can be used to provide the energy necessary for the temperature oscillation. Thermocouples attached to each sample measure the temperature of each sample. Light is used as a radiation source to heat the temperature-modulated sample.

Of interest is Pat. No. 5,688,049 to Gorvorkov, which teaches a device and method for measuring the thermal conductivity of a thin film by determining the change in temperature near the surface of the film after a sample including the film is illuminated with a beam of light. This method is accomplished by modulating the beam of light at a selected modulation frequency and measuring the amplitude of the sound waves created in the gas near the surface of the sample as a result of the repetitive heating and cooling of the surface.

These techniques are all subject to significant limitations. For example, the hot wire technique requires large samples, long times for the sample to come into equilibrium, and an additional long measurement period. The AC and the 3ω techniques require a thin metal film in intimate contact with the sample, with fine electrical contacts to the film. The metal film must be thermally isolated from any heat sink, except for the sample being measured. The combination of film and sample is not mechanically robust, and is not readily separable so that other samples can be measured. The first order transition technique is restricted to the temperatures where materials are available with sharp first order transitions.

Accordingly, it is desirable to provide a simple, rapid and nondestructive technique for measuring the thermal conductivity of low thermal conducting solid materials, particularly one that is sensitive enough to measure the conductivity of materials with K in the range of 0.1–2 W m-1 K-1, and is suitable for on-line control in an industrial production setting and overcomes other drawbacks of the prior art. Since thermal contact cannot be reproduced an improved method to determine the actual thermal contact and the thermal conductivity simultaneously from the heat capacity spectrum from a single measurement is disclosed. No thermal conductivity calibrant is necessary.

The present method determines effective heat capacity Ceff(ω) at different frequencies calculated using a novel step response analysis as a ratio of heat flow rate amplitude AHF and heating rate amplitude Aq. With this model one can thoroughly describe the dynamic behavior of DSC and temperature modulated DSC (TMDSC) systems under conditions of an appreciable temperature gradient inside the sample. A novel algorithm to determine the most important parameters: sample heat capacity, effective thermal contact between the sample and the furnace and finally sample thermal conductivity for the case of real valued heat capacity and thermal conductivity is disclosed.

The present invention provides for quick measurements of small samples for thermal conductivity and heat capacity of the sample are determined simultaneously in a single measurement with the prerequisite that these values are frequency independent. The method is appropriate for state-of-the art power-compensated differential scanning calorimeters without any modification of the measuring system.

Definitions

"Thermal conductivity," as used herein, is the ratio of the heat flow per unit area in the sample to the temperature gradient in the sample.

"Specific heat," as used herein, is the ratio of the change in heat content of a sample of uniform temperature to the product of the change in temperature of the sample and mass of the sample.

"Effective heat capacity," as used herein, is the ratio of the amplitude of the heat flow into a sample to the amplitude of the heating rate applied to the sample at the heat source.

"Thermal contact," as used herein, is the ratio of the heat flow through the sample bottom surface to the temperature difference between furnace and sample.

"Step response analysis", as used herein, is the measurement of heat flow rate and heating rate in time domain.

SUMMARY OF THE INVENTION

The present invention uses known DSC equipment to provide novel techniques for measuring the thermal conductivity of low thermal conducting solid materials, particularly one that is sensitive enough to measure the conductivity of materials with thermal conductivity in the range of about 0.1 W m$^{-1}$ K$^{-1}$ to about 2 W m$^{-1}$ K$^{-1}$.

A system exists in a furnace system where:

| | |
|---|---|
| S | contact area |
| $c_p$ | specific heat capacity of the sample |
| $\rho$ | sample density |
| $\kappa$ | thermal conductivity of the sample |
| d | sample effective thickness (half of the actual thickness for a sample sealed in a pan) |
| $T_s(x,t)$ | sample temperature |
| $T_p(t)$ | pan temperature |
| $T_o(t)$ | furnace temperature |
| $K_{ps}$ | thermal contact between pan and sample |
| $K_{op}$ | thermal contact between furnace and pan |
| $\Phi_p(t)$ | heat flow rate into the sample |

It is the object of the present invention to teach a method to determine simultaneously thermal conductivity, the thermal contact and heat capacity of low thermal conducting materials like polymers. No additional measurements, no thermal conducting calibrants, and no modifications of the commercially available DSC are necessary.

It is the object of the present invention to provide a method based on temperature waves propagation through the sample. At low frequencies of perturbation temperature waves go through whole sample without damping, the whole sample is modulated and, therefore, large effective heat capacity is measured. At higher frequencies, temperature waves are damped and the sample is modulated only partly. Thus, measured effective heat capacity is smaller. The damping is stronger for poor thermal conducting materials.

It is the object of the present invention to provide a method, which overcomes the disadvantage of known techniques for measuring thermal contact.

It is the object of the present invention to provide a method, which determines the actual thermal contact and the thermal conductivity simultaneously from a heat capacity spectrum from a single measurement. No thermal conductivity calibrant is necessary.

It is the object of the present invention to provide a method for measuring thermal conductivity where heat capacity of the sample is measured at different frequencies. Low frequency temperature waves go through the whole sample without damping, the whole sample is modulated and therefore, a large apparent heat capacity is measured. Higher frequency temperature waves are damped and the sample is partly modulated—the measured apparent heat capacity is smaller. The damping is stronger for poor thermal conducting materials. However, the same damping effect appears by finite thermal contact (heat transfer coefficient) between the sample surface and the furnace—a poor thermal contact damps the temperature waves more strongly than a good one. But the thermal contact and thermal conductivity lead to different frequency dependencies of apparent heat capacity. This difference allows the necessary separating of damping effects due to the thermal contact and due to the thermal conductivity. Moreover, it is not necessary to measure apparent heat capacity at different frequencies with TMDSC. The spectrum of temperature waves can be easily generated by a single step in the program temperature.

In the preferred embodiment of this invention, known DSC apparatuses are utilized, and may be simplified to cases where a solid sample is measured directly in a DSC furnace. Three parameters need to be determined: specific heat capacity, effective thermal contact between the sample and the furnace (K), and thermal conductivity ($\kappa$).

It is the object of the present invention to provide a method of measuring thermal conductivity of a sample where effective heat capacity $C_{eff}(\omega)$ at different frequencies can be calculated from step response analysis as a ratio of heat flow rate amplitude $A_{HF}$ and heating rate amplitude $A_q$:

$$C_{eff}(\omega) = \frac{A_{HF}}{A_q} = \frac{\sum_{i=1}^{n} HF_i \cos(\omega t_i) - i \sum_{i=1}^{n} HF_i \sin(\omega t_i)}{\sum_{i=1}^{n} q_i \cos(\omega t_i) - i \sum_{i=1}^{n} q_i \sin(\omega t_i)} \quad (1)$$

where points of heat flow rate, $HF_i$, and heating rate, $q_i$, should be taken both with the same sampling rate (number of points per unit time). Points are collected from the beginning of the temperature step until the heat flow reaches the steady state value at the isotherm, having in total n points. After that the $C_{eff}(\omega)$ values are corrected for apparatus influence (instrumental delay) as:

$$C_{app}(\omega) = C_{eff}(\omega) \cdot B_2(\omega) \quad (2)$$

where $C_{app}(\omega)$ is an apparent heat capacity at frequency $\omega$, and $B_2(\omega)$ is the dynamic calibration factor of the instrument.

It is the object of the present invention to provide a method of measuring thermal conductivity where the first parameter of the system, the specific heat capacity $c_p$, can easily be determined as $$c_p = \frac{C_{eff}(0)}{m_s} \quad (3)$$

where $m_s$ is the sample mass and $C_{eff}(0)$ is calculated from Eg. (1) for $\omega=0$.

It is the object of the present invention to provide a method of measuring thermal conductivity where apparent heat capacity is given as $$C_{app}(\omega) = \frac{C_\alpha(\omega)}{1 - \frac{i\omega}{K} C_\alpha(\omega)} \quad (4)$$

where $C_\alpha(\omega)$ is the apparent heat capacity in a case of ideal thermal contact between the sample and the furnace. Apparent heat capacity is measured directly on the bottom surface of the sample.

Equation (4) from above can be re-written as:

$$C_\alpha(\omega) = \frac{C_{app}(\omega)}{1 + \frac{i\omega}{K} C_{app}(\omega)} \quad (5)$$

Unknown parameter in Eq. (5) is K because $C_{app}(\omega)$ is measured by DSC. The lower the frequency $\omega_k$ the larger the modulus of $C_{app}(\omega_k)$ and $C_\alpha(\omega_k)$.

It is the object of the present invention to provide a method of measuring thermal conductivity where the second parameter (effective thermal contact of said sample) of the system is determined by describing $C_\alpha(\omega)$ on a solid curve. The theoretical $C_\alpha(\omega)$ curve in a polar plot representation depends only on the value $C_\alpha(\omega=0)$, that is sample true heat capacity $c_p{}^*m_s$, and does not depend on all other parameters. The correct value for K is then the value at which all $C_\alpha(\omega_k)$ points, calculated by Eq. (5), lie on the theoretical curve.

It is the object of the present invention to provide a method of measuring thermal conductivity where sample thermal conductivity $\kappa$ is readily determined.

$$C_\alpha(\omega) = -\frac{1}{i\omega} \kappa \cdot S \cdot \alpha \tanh(\alpha \cdot d) \quad (6)$$

where all measured parameters, except thermal conductivity $\kappa$, are known (density $\rho$ can be calculated from the sample mass and sample size, which are set before measurement). At any given frequency $\omega_k \neq 0$ increasing of $\kappa$ leads to shifting the position of the $C_\alpha(\omega_k)$ point on the theoretical curve towards $C_\alpha(\omega=0)$.

It is the object of the present invention to provide a method of measuring thermal conductivity where by varying $\kappa$ in $$C_\alpha(\omega) = -\frac{1}{i\omega} \kappa \cdot S \cdot \alpha \tanh(\alpha \cdot d) \quad (6)$$

the condition is reached where the same set of $\omega_k$ calculated $C_\alpha(\omega_k)$ points coincide with measured points $C_\alpha(\omega_k)$, determined by Eq. (5).

The measured points for $C_\alpha(\omega_k)$ will not exactly coincide with theoretical ones, rather a scatter corresponding to only about 1 to about 2 percent uncertainties in determination of thermal conductivity ($\kappa$) and effective thermal contact (K) is produced.

DETAILED DESCRIPTION

The present invention resides in control methods for conventional differential analytical apparatus, and is an improvement on the methods currently practiced to control such conventional differential analytical apparatus.

The following detailed description of the present invention applies specifically to differential scanning calorimetry (DSC), in which temperature is the driving variable and heat flow is the characterizing differential physical parameter. However, although the present invention is described as applied to differential scanning calorimetric analysis, it should be understood that the present invention could be used with any differential thermal analysis method including Pressure Differential Scanning Calorimetry, Differential Thermal Analysis, Pressure Differential Thermal Analysis, Differential Photocalorimetry, Pressure Differential Photocalorimetry, Differential Thermogravimetry, and Pressure Differential Thermogravimetry, as well as any combination of these techniques. The principles and methods described herein with reference to differential scanning calorimetric analysis could be applied to any and all of the thermal analytical methods listed above, as well as to other analytical methods wherein a characterizing differential physical parameter is measured as a function of a driving variable.

The System

Figure 1B:
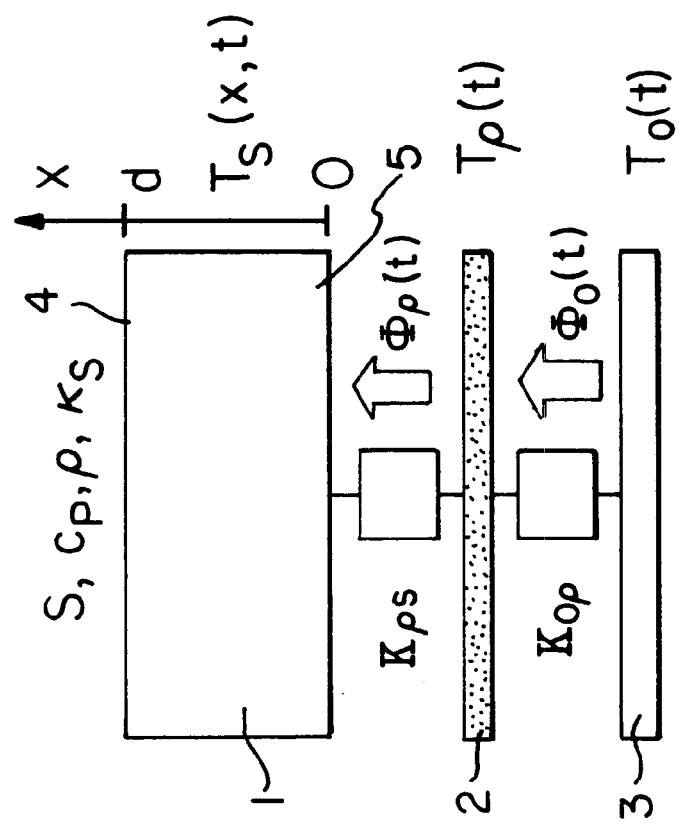
FIGS. 1(a) and 1(b) are a schematic view of the furnace (a) and its block diagram (b).
Figure 1A:
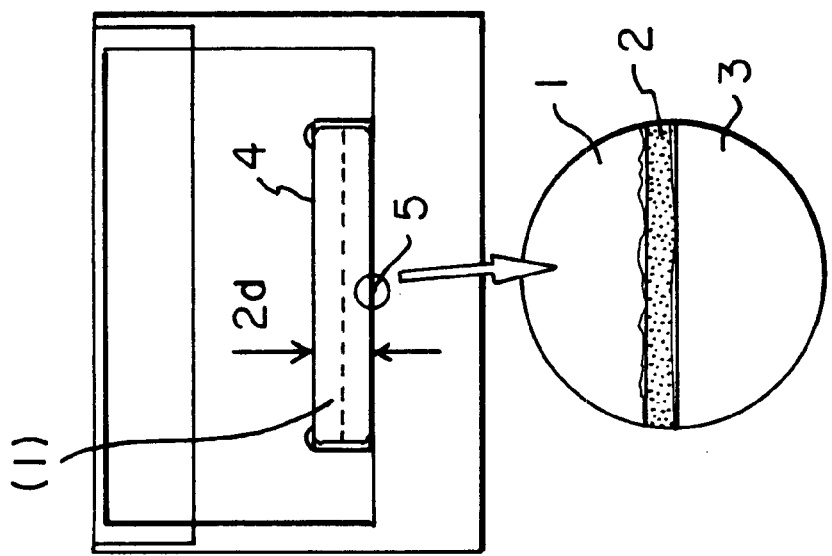

FIG. 1a is a schematic representation of the present invention as it may be used with known Differential Scanning Calorimetry (DSC) (3), for example, Perkin-Elmer Pyris-1 DSC. Differential scanning calorimeter furnace (3) consists of a sample (1) which is preferably in disc formation, and a grease layer (2). Sample (1) may be any type of sample, however the present invention is appropriate for low thermal conducting solid materials, for examples polymers. Low thermal conducting means a material has a thermal conductivity value K in the range of about 0.1–2 W m−1 K−1. Typical polymers include polystyrene, poly (methyl methacrylate), and epoxy resins. Grease layer (2) produces an effective amount of thermal contact. In general, utilizing greater amounts of grease (2) in this method produces a better thermal contact. In the preferred embodiment of this invention about 0.5 to about 1 mg of grease (2) is applied to the sample.

FIG. 1 also shows adiabatic layer (4) located at the upper surface of sample (1). The bottom of sample (1) is represented as (5) and is opposite adiabatic layer (4). FIG. 1b shows a block diagram of the same conventional differential scanning calorimeter furnace (3).

FIGS. 1a and 1b show schematic representation of a typical sample furnace system where:

| | |
|---|---|
| S | contact area |
| $c_p$ | specific heat capacity of the sample |
| ρ | sample density |
| κ | thermal conductivity of the sample |
| d | sample effective thickness (half of the actual thickness for a sample sealed in a pan) |
| $T_s(x,t)$ | sample temperature |
| $T_p(t)$ | pan temperature |
| $T_o(t)$ | furnace temperature |
| $K_{ps}$ | thermal contact between pan and sample |
| $K_{op}$ | thermal contact between furnace and pan |
| $\Phi_p(t)$ | heat flow rate into the sample |
| $\Phi_o(t)$ | heat flow rate into the pan-sample system |

The Theory

Solving the heat transfer equation for a model of FIGS. 1a and 1b, a relatively thin sample can be considered as a one-dimensional system, where the expression for the apparent heat capacity $C_{app}(\omega)$ of the sample-pan-furnace system is:

$$C_{app}(\omega) = \frac{C_{pan} + C_\beta(\omega)}{1 - \frac{i\omega}{K_{op}}(C_{pan} + C_\beta(\omega))} \quad (7)$$

where $C_{pan}$ is the heat capacity of the pan, $$C_\beta(\omega) = \frac{C_\alpha(\omega)}{1 - \frac{i\omega}{K_{ps}}C_\alpha(\omega)}, \quad (8)$$

denotes the apparent heat capacity which would be measured directly at the surface of the sample pan and $$C_\alpha(\omega) = -\frac{1}{i\omega}\kappa \cdot S \cdot \alpha\tanh(\alpha \cdot d), \quad (9)$$

denotes the apparent heat capacity which would be measured directly at the surface of the sample, $$\alpha = \sqrt{\frac{\omega}{|\chi|}}\exp\left\{\frac{i}{2}arg\left(-i\frac{\omega}{\chi}\right)\right\}, \chi = \frac{\kappa}{\rho \cdot c_p}$$

is the thermal diffusivity. Eq. (7–9) are complex and valid also for complex frequency dependent thermal conductivity ($\kappa$) and Specific heat capacity ($c_p$).

For the method of thermal conductivity determination it is assumed that $\kappa$ and $c_p$ are real valued and frequency independent. The sample-pan-furnace system may be simplified by excluding the pan. The sample disk is measured directly in the DSC furnace. In this case the sample disk is heated only from bottom layer (5), therefore an adiabatic layer (4) is assumed at the upper surface of the sample (1). Effective sample thickness d is then the actual sample thickness and the contact area S is the bottom surface area of the disk.

In Eq. (7) setting $C_{pan}=0$ and $K_{op}\to\infty$ leads to $C_{app}(\omega)=C_\beta(\omega)$. Eq. (7) is rewritten as:

$$C_{app}(\omega) = \frac{C_\alpha(\omega)}{1 - \frac{i\omega}{K}C_\alpha(\omega)}. \quad (10)$$

where now K is the effective thermal contact between the bottom sample surface and the furnace.

FIGS. 1a and 1b show the preferred DSC setup of the present invention where a solid sample is measured directly in the DSC furnace. Three parameters need to be determined: specific heat capacity ($c_p$), effective thermal contact between the sample and the furnace (K) and thermal conductivity ($\kappa$).

The preferred method is to determine the effective heat capacity $C_{eff}(\omega)$ at different frequencies, generating a heat capacity spectrum.

The preferred method of step response analysis in DSC allows the fast generation of heat capacity spectra. In common temperature modulated calorimetry, like 3$\omega$-method, AC-calorimetry and temperature modulated differential scanning calorimetry (TMDSC), periodic perturbations are used to determine dynamic heat capacity. In contrast, this method uses a single step in program temperature followed by an isothermal segment to obtain the spectrum of heat capacity. To follow system evolution with time or temperature one can repeat the temperature step several times also in a non-periodic manner (for example, like in StepScan-DSC™ PerkinElmer Instruments). Heating rate and measured heat flow rate are evaluated in time domain. With this method it is possible to cover more than two orders of magnitude in frequency in a single measurement. This allows a dramatic shortening of the measuring time compared to temperature modulated DSC.

The preferred method of generating frequency dependent quantities by DSC is where the programmed temperature undergoes a sharp single step followed by an isothermal segment. To follow system evolution with time or temperature one can repeat the temperature step several times also in a non-periodic manner. Heating rate and measured heat flow rate are evaluated in time domain by Laplace transformation to obtain the heat capacity spectrum.

$C_{eff}(\omega)$ is an effective (apparent) heat capacity of the measured system (which measured by the instrument), which reads:

$$C_{eff}(\omega) = \frac{A_{HF}(\omega)}{i\omega A_T(\omega)} = \frac{A_{HF}(\omega)}{A_q(\omega)} \quad (11)$$

where $A_{HF}(\omega)$ is a heat flow rate amplitude, $A_T(\omega)$ is a temperature amplitude, $A_q(\omega)$ is a heating rate amplitude.

One can further calculate from that value the true sample heat capacity by means of a calibration procedure but it is not an essential point for our consideration here. The important point is that the heat capacity at frequency $\omega$ can be calculated only at a non-zero heating rate amplitude $A_q(\omega)$, which means that the heating rate q(t) should have a periodic component with frequency $\omega$. If the instrument has such a sampling rate, that we get n points per period for HF(t) and q(t) signals, Eq. (11) can be rewritten as:

$$C_{eff}(\omega) = \frac{\sum_{i=1}^{n} HF_i\cos(\omega t_i) - i\sum_{i=1}^{n} HF_i\sin(\omega t_i)}{\sum_{i=1}^{n} q_i\cos(\omega t_i) - i\sum_{i=1}^{n} q_i\sin(\omega t_i)}. \quad (1)$$

The periodic heating rate q(t) should contain a delta function to generate an uniform heat flow rate spectrum (i.e. equal $A_q(\omega_k)$ at different frequencies $\omega_k=k^*\omega_0$, $\omega_0=2\pi/t_p$, $t_p$ is the basic period of q(t), k is integer). Then the temperature-time profile should have infinite sharp stepwise changes.

Figure 2A:
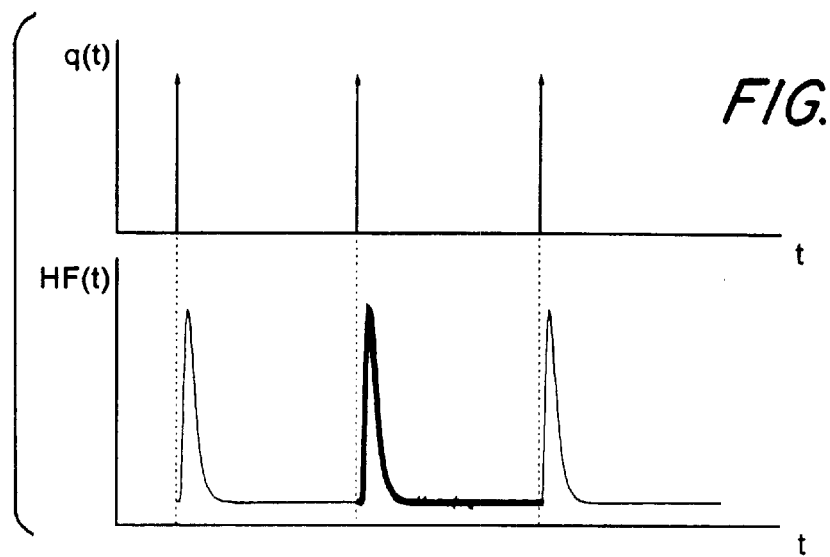
FIG. 2(a) shows heating rate q(t) as a delta function and the corresponding heat flow rate HF(t) for periodic heating rate (part a)

FIG. 2(a) shows a single period of a heating rate function with respect to heat flow rate. If the period between pulses is long enough then the heat flow rate reaches the steady state value before the next temperature step. Since the heat flow rate is periodic, each peak in the heat flow rate starts from the same steady state value. One may set the steady state value of the heat flow rate to zero without influencing the amplitudes of all harmonics. The same can be done with the heating rate.

Figure 2B:
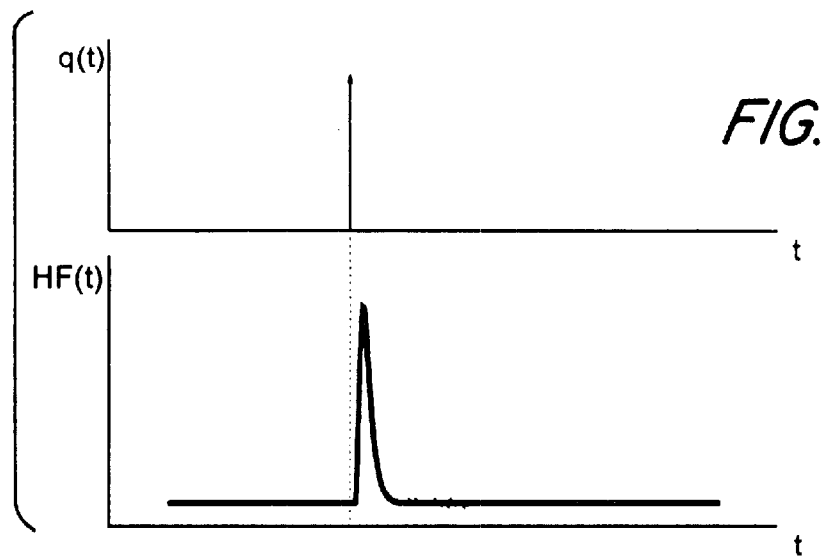
FIG. 2(b) shows a single heating rate pulse.
Figure 2C:
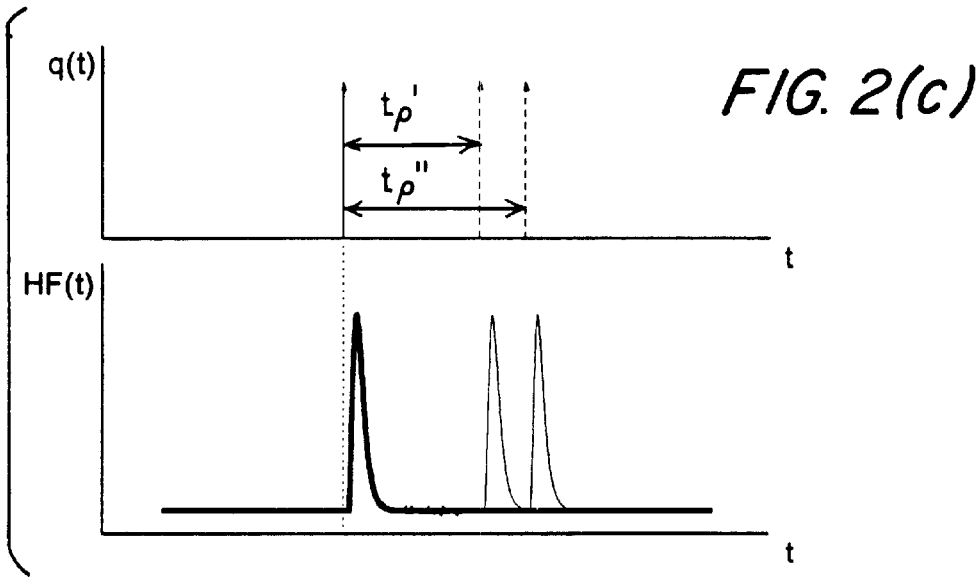
FIG. 2(c) shows a single heating rate pulse, which can be followed by another pulse after the time interval $t_p'$ or $t_p''$.

Since we have a steady state part of the heat flow rate before the peak, the peak itself does not "feel" the previous peaks. Consequently the shape of the peak is exactly the same as that of a single peak measured with only one heating rate pulse, see FIG. 2(b). One may treat this single peak as a single period of some fictitious periodic function with basic period $t_p'$ or $t_p''$, see FIG. 2(c), and calculate $C_{eff}(\omega)$ at the set of frequencies $\omega'_k=k^*2\pi/t'_p$ or $\omega''_k=k^*2\pi/t''_p$. The shortest possible basic period $t_{p\ min}$ of such function is the time the heat flow rate returns back to the steady state value after the perturbation. The longest basic period $t_{p\ max}$ is the time interval the heat flow rate has been actually measured after the temperature step. Since one may vary the basic period in a certain range for this single step in temperature one may generate a continuous spectrum of heating rate instead of a discreet spectrum in case of the periodic q(t). Then $C_{eff}(\omega)$ can be calculated for a continuous frequency range $\omega \geq 2\pi/t_{p\ max}$.

Preferably one may start the Fourier integration just at the position of the delta function (for real measurements—at the beginning of the temperature step) and integrate over the whole period $t_p'$ or $t_p''$. In fact heat flow rate does not contribute to the Fourier integral any more after its relaxation back to the steady state value. Then the only variable for $C_{eff}(\omega)$ determination is the frequency $\omega$.

Finally the data treatment becomes nothing else as an operational calculus. The complicated relation in time domain between heat flow rate and heating rate, which is given by a convolution product, can be resolved using the Laplace transformation $$L(p) = \int_0^{+\infty} f(t)e^{-pt}dt \tag{12}$$

where variable p can be any complex number and f(t) represents heating rate q(t) and heat flow rate HF(t). We can set p=iω and choose the time scale so that t=0 at the very beginning of the temperature step. One may calculate Laplace transformed of the heating rate q(t) and the heat flow rate HF(t) as:

$$L(i\omega) = \int_0^{+\infty} f(t)e^{-i\omega t}dt = \int_0^{t_p'} f(t)e^{-i\omega t}dt \tag{13}$$

because remaining integral $$\int_{t_p'}^{+\infty} f(t)e^{-i\omega t}dt \tag{14}$$

equals zero for both q(t) and HF(t) (remember that we set the steady state values of q(t) and HF(t) to zero by subtracting the constant offset values). The effective heat capacity we can determine as follows:

$$C_{eff}(\omega) = \frac{\int_0^{t_p'} HF(t)e^{-i\omega t}dt}{\int_0^{t_p'} q(t)e^{-i\omega t}dt} \tag{15}$$

Next the integration limits are fixed and only the frequency ω varies to get the heat capacity spectrum. If one where to sample n points of heat flow rate and of heating rate during the time interval (0, $t_p'$) the integrals can be changed to sums and Eq. (15) equals exactly Eq. (1), since $e^{-i\omega t}=\cos(\omega t)-i\sin(\omega t)$. Further for real measurement we use Eq. (1).

The area under the heat flow rate peak in time domain is the total amount of heat absorbed by the sample due to the stepwise increase of temperature. This heat equals the numerator in Eq. (15) for ω=0, that is then simply integral $$\int_0^{t_p'} HF(t)dt,$$

and the height of the temperature step equals to denominator. Therefore $C_{eff}(0)$, calculated by Eq. (15) or Eq. (1) for ω=0, corresponds to the total heat capacity.

Since the single step measurement can be analyzed as a fictitious periodic measurement under condition that q(t) and HF(t) start and end at the same steady state values. Therefore to get correct $C_{eff}(\omega)$ values by Eq. (1) the measurements should start from steady state. The step in temperature can be approximated as a very steep heating (or cooling) ramp in short time. For example we have used a programmed heating rate of 75 K/min for 0.8 second and 1.6 second to have 1 K and 2 K temperature steps, respectively. After the temperature step the heat flow rate HF(t) should be recorded until it returns back to steady state.

The measured step in the temperature-time profile is not as sharp as it was programmed because of instrumental delay. The power compensated system having much smaller furnaces than the heat flux system, responds much faster and follows more tightly the program temperature. For $C_{eff}(\omega)$ determination by Eq. (1) a large part of the instrumental delay can be eliminated by using the measured heating rate instead of programmed one.

$C_{eff}(\omega)$ values, calculated by Eq. (1) correspond to some average values of actual $C_{eff}(\omega)$ spectrum in the temperature range $(T_0, T_0+\Delta T)$ and in the time interval $(t_0, t_0+t_{p\ max})$, where $T_0$ is the starting temperature of the step measurement, $\Delta T$ is the height of the temperature step, $t_0$ is the starting time, $t_{p\ max}$ is the total measuring time of the single step. One may monitor the evolution of the $C_{eff}(\omega)$ spectrum with changing temperature or with time (e.g. during isothermal crystallization), one can repeat the step perturbation at another temperature or at another time.

Therefore, the effective heat capacity $C_{eff}(\omega)$ at different frequencies is preferably calculated from step response analysis as a ratio of heat flow rate amplitude $A_{HF}$ and heating rate amplitude $A_q$:

$$C_{eff}(\omega) = \frac{A_{HF}}{A_q} = \frac{\sum_{i=1}^n HF_i \cos(\omega t_i) - i\sum_{i=1}^n HF_i \sin(\omega t_i)}{\sum_{i=1}^n q_i \cos(\omega t_i) - i\sum_{i=1}^n q_i \sin(\omega t_i)} \tag{1}$$

where points of heat flow rate, $HF_i$, and heating rate, $q_i$, are preferably taken both with the same sampling rate (number of points per unit time). Preferably the points are collected from the beginning of the temperature step until the heat flow reaches the steady state value at the isotherm, having in total n points. After that the $C_{eff}(\omega)$ values should be corrected for apparatus influence (instrumental delay) as:

$$C_{app}(\omega) = C_{eff}(\omega) \cdot B_2(\omega) \tag{2}$$

where $C_{app}(\omega)$ is an apparent heat capacity at frequency ω, and $B_2(\omega)$ is the dynamic calibration factor of the instrument.

Preferably, the first parameter of the system, the specific heat capacity $c_p$, can be easily determined as:

$$c_p = \frac{C_{eff}(0)}{m_s} \tag{3}$$

where $m_s$ is the sample mass and $C_{eff}(0)$ is calculated from Eg. (1) for ω=0.

In the preferred method of measuring thermal conductivity apparent heat capacity is given as:

$$C_{app}(\omega) = \frac{C_a(\omega)}{1 - \frac{i\omega}{K}C_a(\omega)} \tag{4}$$

where $C_a(\omega)$ is the apparent heat capacity in a case of ideal thermal contact between the sample and the furnace. It is the apparent heat capacity which is measured directly on the bottom surface of the sample.

Equation (4) from above can be re-written as:

$$C_a(\omega) = \frac{C_{app}(\omega)}{1 + \frac{i\omega}{K} C_{app}(\omega)} \quad (5)$$

Unknown parameter in Eq. (5) is K because $C_{app}(\omega)$ is measured by DSC. The lower the frequency $\omega_k$ the larger the modulus of $C_{app}(\omega_k)$ and $C_a(\omega_k)$.

In the preferred method of measuring thermal conductivity the second parameter of the system is determined by describing $C_a(\omega)$ on a solid curve. The theoretical $C_a(\omega)$ curve in a polar plot representation depends only on the value $C_a(\omega=0)$, that is sample true heat capacity $c_p * m_s$, and does not depend on all other parameters. The correct value for K is then the value at which all $C_a(\omega_k)$ points, calculated by Eq. (5), lie on the theoretical curve.

Figure 3:
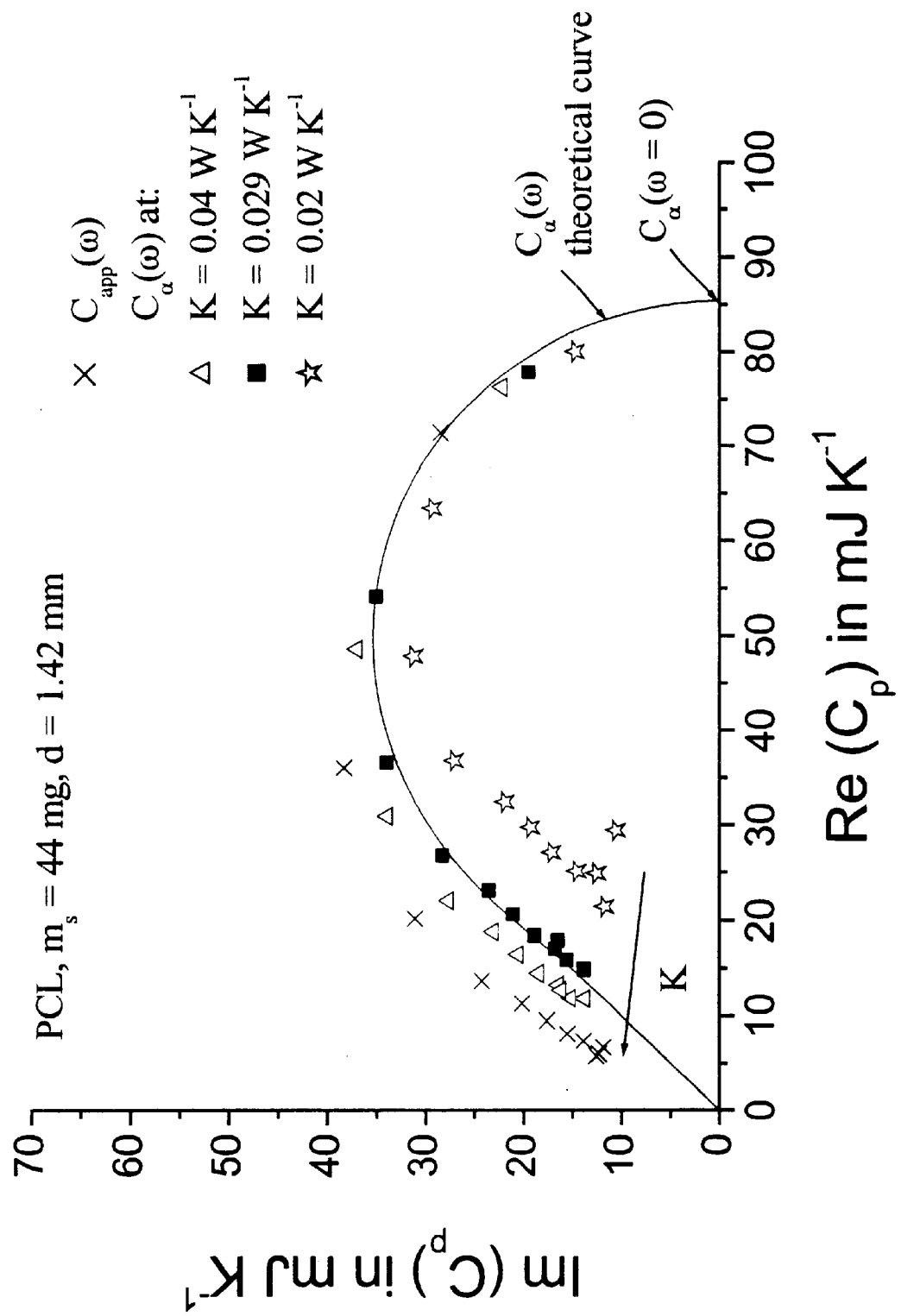
FIG. 3 shows a polar plot of $C_{app}(\omega_k)$ and $C_\alpha(\omega_k)$ for effective thermal contact K. The horizontal and vertical axes show the real and imaginary parts, respectively. Solid curve is theoretical values of $C_\alpha(\omega)$ for given $C_\alpha(\omega=0)$.

FIG. 3 shows values of $C_{app}(\omega_k)$ for a set of different frequencies $\omega_k$ and $C_a(\omega_k)$ for three different values of K at 0.04 W K$^{-1}$, 0.029 W K$^{-1}$, and 0.02 W K$^{-1}$. A polar plot of $C_{app}(\omega_k)$ and $C_a(\omega_k)$ for effective thermal contact K is shown for PCL where m is equal to 44 mg and d=1.42 mm. The horizontal and vertical axes show the real and imaginary parts, respectively. Solid curve is theoretical values of $C_a(\omega)$ for given $C_a(\omega=0)$. Since the correct value for K is the value at which all $C_a(\omega_k)$ points, calculated by Eq. (5), lie on the theoretical curve. In this case K=0.029 W K$^{-1}$.

The preferred method of measuring thermal conductivity where sample thermal conductivity κ is readily determined by:

$$C_a(\omega) = -\frac{1}{i\omega} \kappa \cdot S \cdot \alpha \tanh(\alpha \cdot d) \quad (6)$$

where all parameters, except thermal conductivity κ, are known (density ρ can be calculated from the sample mass and sample size, which are set before measurement). At any given frequency $\omega_k \neq 0$ increasing of κ leads to shifting the position of the $C_a(\omega_k)$ point on the theoretical curve towards $C_a(\omega=0)$.

The preferred method of measuring thermal conductivity where by varying κ in:

$$C_a(\omega) = -\frac{1}{i\omega} \kappa \cdot S \cdot \alpha \tanh(\alpha \cdot d) \quad (6)$$

the condition is reached where the same set of $\omega_k$ calculated $C_a(\omega_k)$ points coincide with measured points $C_a(\omega_k)$, determined by Eq. (5).

Figure 4:
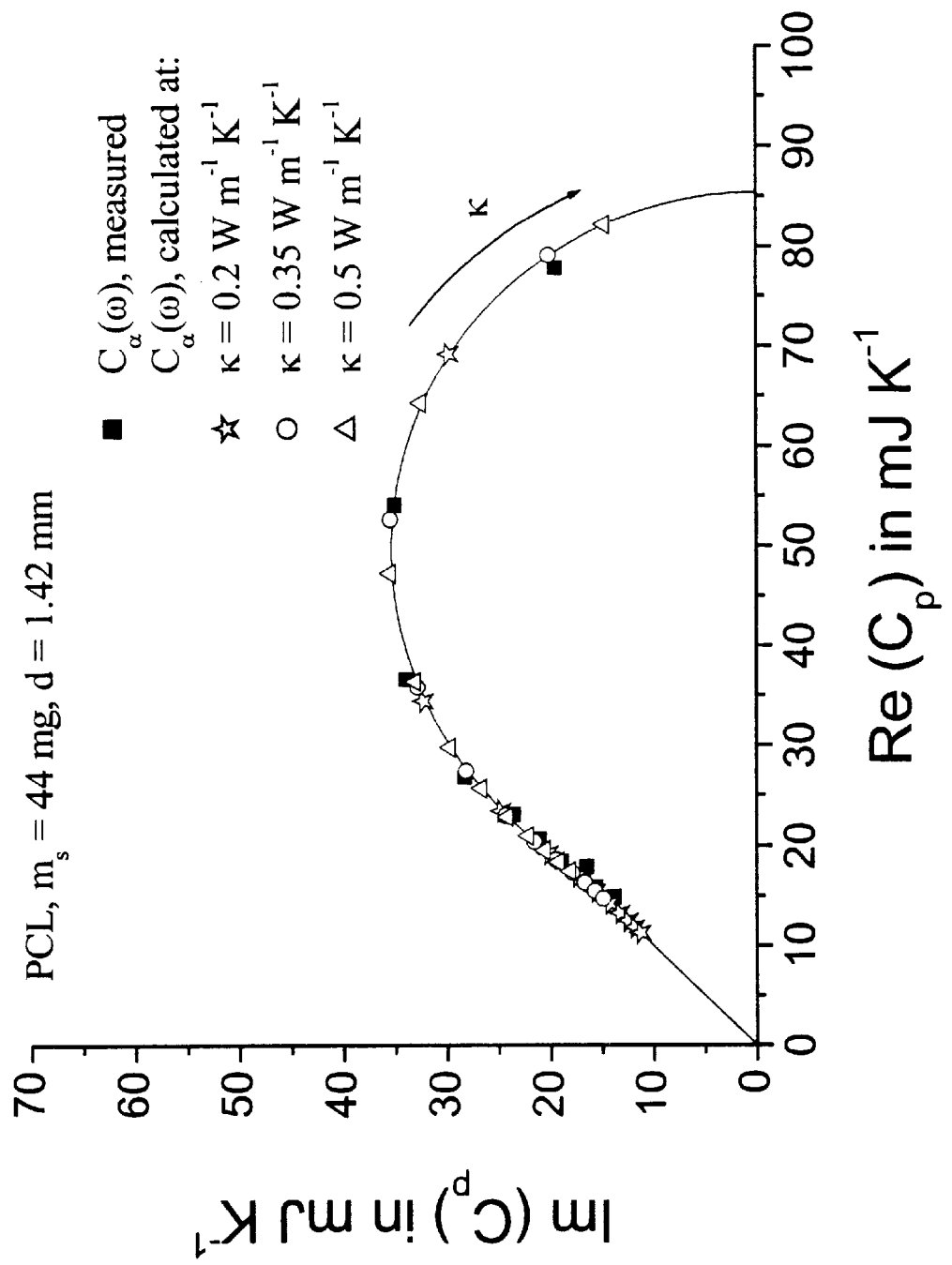
FIG. 4 shows a polar plot of $C_\alpha(\omega_k)$, measured and calculated for different values of thermal conductivity κ. The horizontal and vertical axes show the real and imaginary parts, respectively.

FIG. 4 shows a polar plot of $C_a(\omega_k)$, measured and calculated for different values of thermal conductivity κ. The horizontal and vertical axes show the real and imaginary parts, respectively. By varying κ in Eq. (6) the condition is reached where the same set of $\omega_k$ calculated $C_a(\omega_k)$ points coincide with measured points $C_a(\omega_k)$, determined by Eq. (5). In this case for PCL where m is equal to 44 mg and d=1.42 mm it happens at κ=0.35 W m$^{-1}$ K$^{-1}$.

Figure 5:
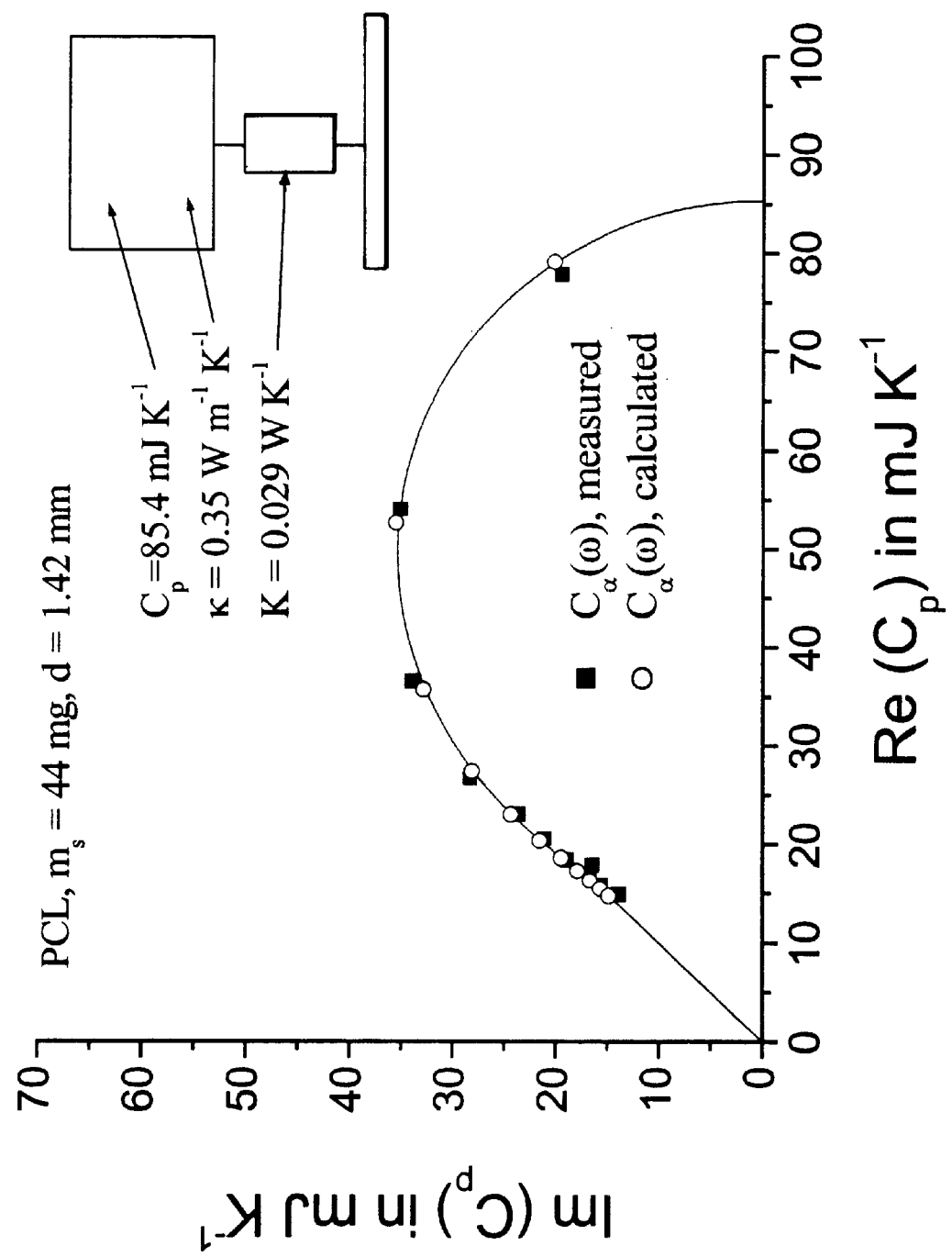
FIG. 5 shows a polar plot of $C\alpha(\omega k)$, calculated with optimal parameter κ and measured. The horizontal and vertical axes show the real and imaginary parts, respectively.

FIG. 5 shows that the measured points for $C_a(\omega_k)$ will not exactly coincide with theoretical ones, rather a scatter corresponding to only about 1 to about 2 percent uncertainties in determination of thermal conductivity (κ) and effective thermal contact (K) is produced in this case for PCL where m is equal to 44 mg and d=1.42 mm.

The algorithm to determine thermal conductivity and effective thermal contact from the spectrum of $C_{app}(\omega_k)$ is realized on MS-Excel™ spreadsheet with Visual Basic™ macros.

Figure 6:
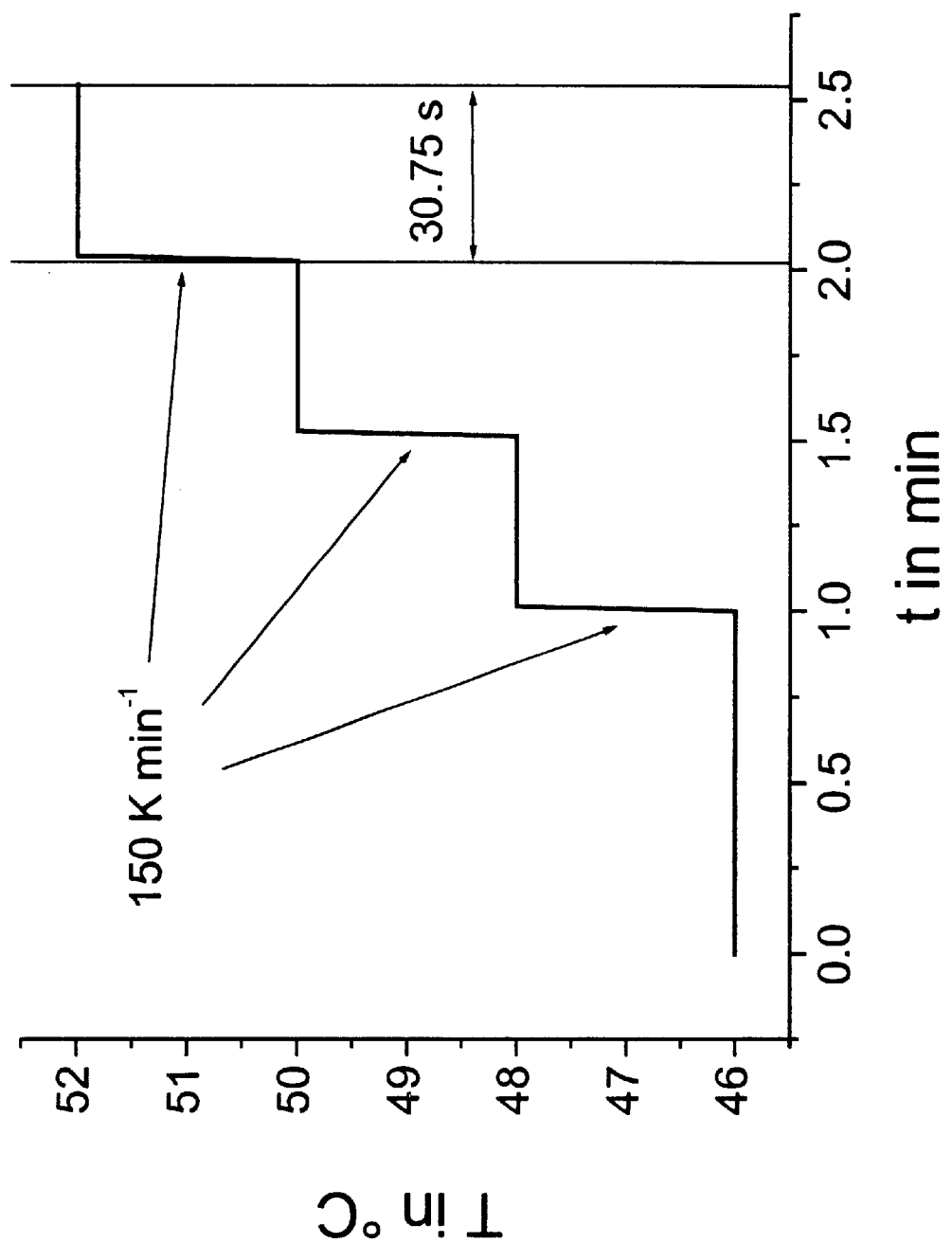
FIG. 6 shows a temperature-time program, consisting of 2 K steps in temperature and 30 s isotherms. Temperature steps were programmed as short heating segments with 150 K min−1 heating rate.

FIG. 6 shows a temperature-time program, consisting of 2 K steps in temperature and 30 s isotherms. Temperature steps were programmed as short heating segments with 150 K min−1 heating rate. Temperature-time program shown in FIG. 6 was used to generate the spectrum of apparent heat capacities in the examples below.

Figure 7:
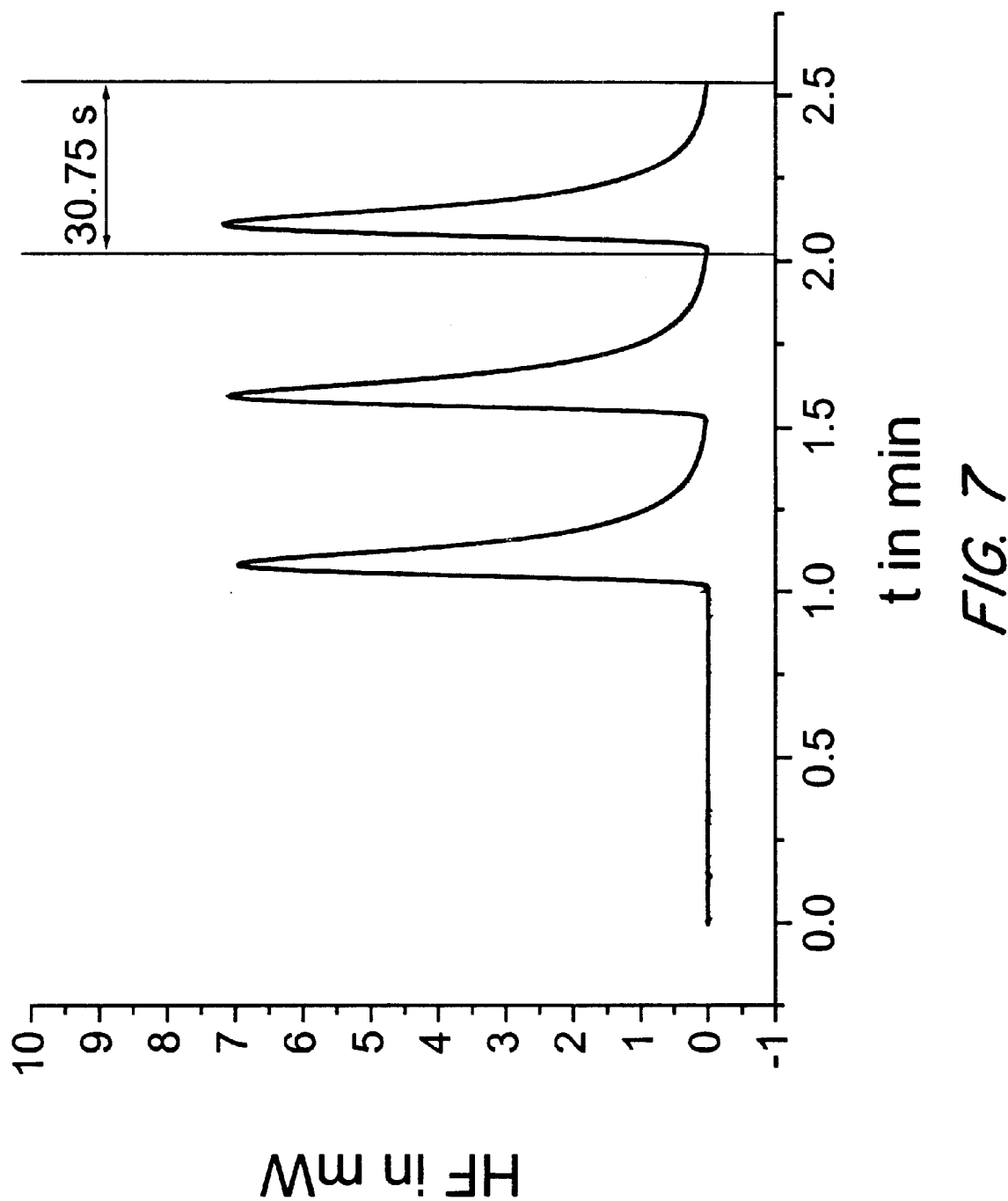
FIG. 7 shows an example of measured heat flow rate HF versus time which corresponds to the temperature-time program, shown in FIG. 4. The last peak was taken for further data evaluation.

FIG. 7 shows an example of measured heat flow rate HF versus time which corresponds to the temperature-time program, shown in FIG. 6. The last peak was taken for further data evaluation. Initial isotherm of 1 min was added to check whether heat flow drift at steady state is remarkable. FIG. 7 shows corresponding heat flow rate after empty furnace correction is shown. (Since we did not use a pan we subtracted the heat flow measured with an empty furnace.)

Figure 8A:
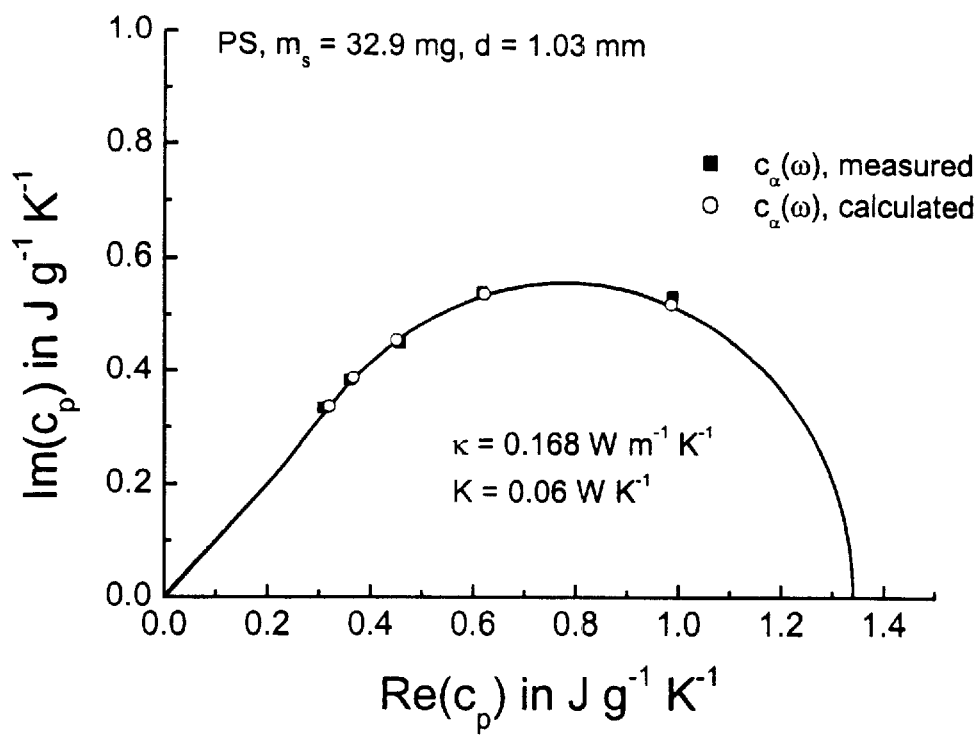
FIG. 8 shows a polar plot of $C_\alpha(\omega_k)$, measured and calculated, for PS disks with thickness 1.03 mm (a) and 0.44 mm (b). The horizontal and vertical axes show the real and imaginary parts, respectively.
Figure 8B:
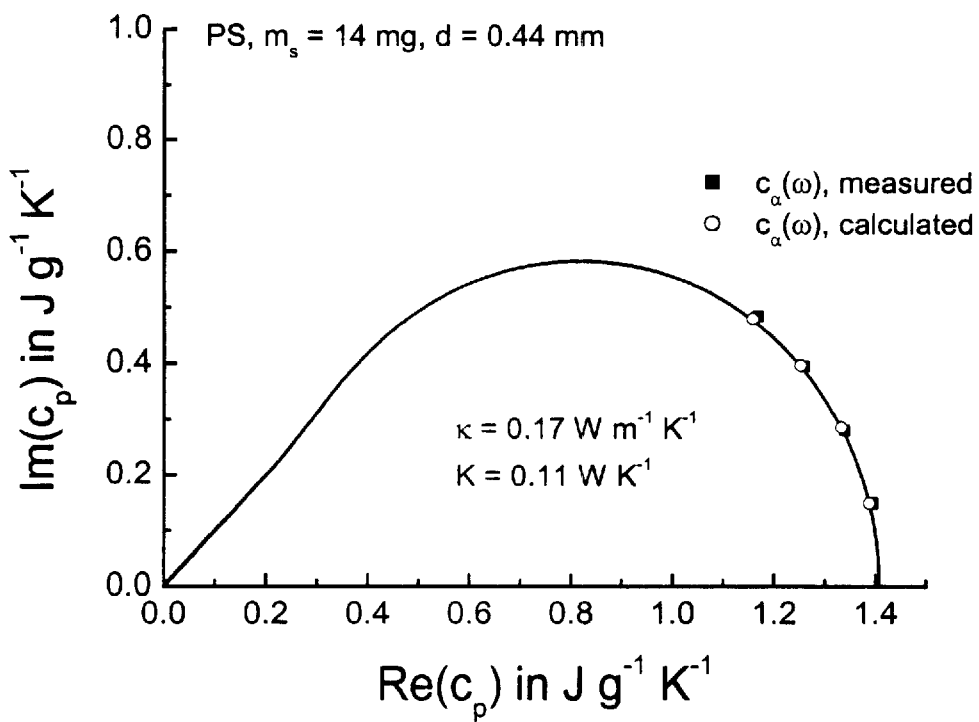

FIG. 8 shows a polar plot of $C_a(\omega_k)$, measured and calculated, for PS disks with thickness 1.03 mm (a) and 0.44 mm (b). The horizontal and vertical axes show the real and imaginary parts, respectively. Two PS disks with different thickness give quite different values of $C_a(\omega_k)$ at the same set of frequencies. However both sets of $C_a(\omega_k)$ give almost the same value of thermal conductivity κ of about 0.17 W m$^{-1}$ K$^{-1}$ that is the property of the material.

Figure 9A:
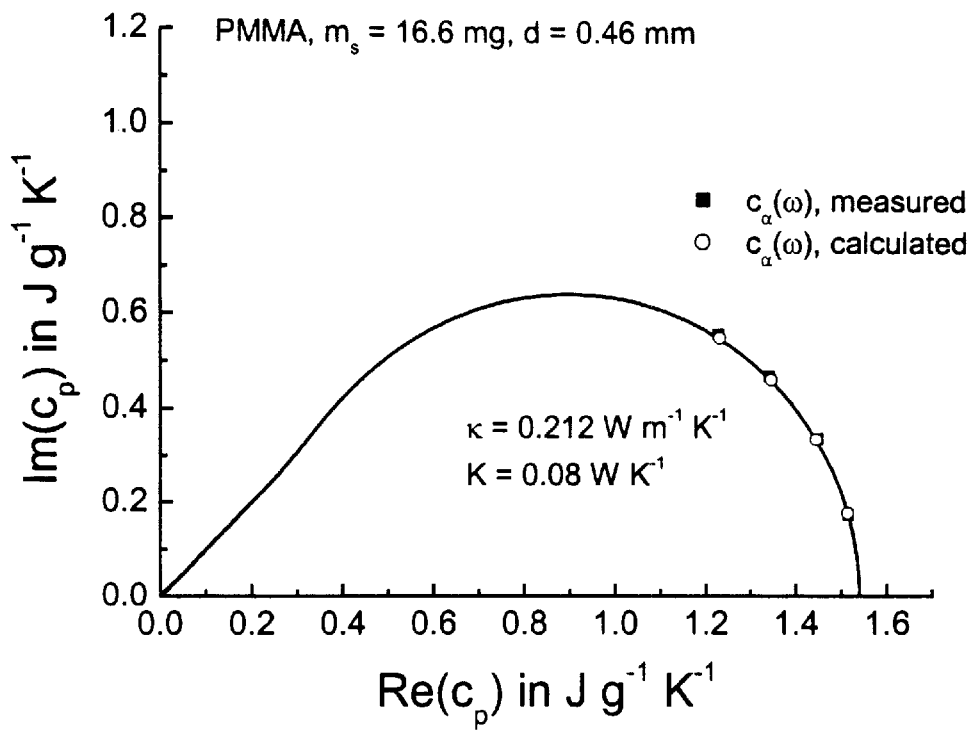
FIG. 9 shows a polar plot of $C_\alpha(\omega_k)$, measured and calculated, for PMMA disks with thickness 0.46 mm (a) and 1.052 mm (b). The horizontal and vertical axes show the real and imaginary parts, respectively. In part (b) $C_\alpha(\omega_k)$ values are shown for two different effective thermal contacts K=0.035 W K$^{-1}$ and K=0.11 W K$^{-1}$ and slightly different $c_p$.
Figure 9B:
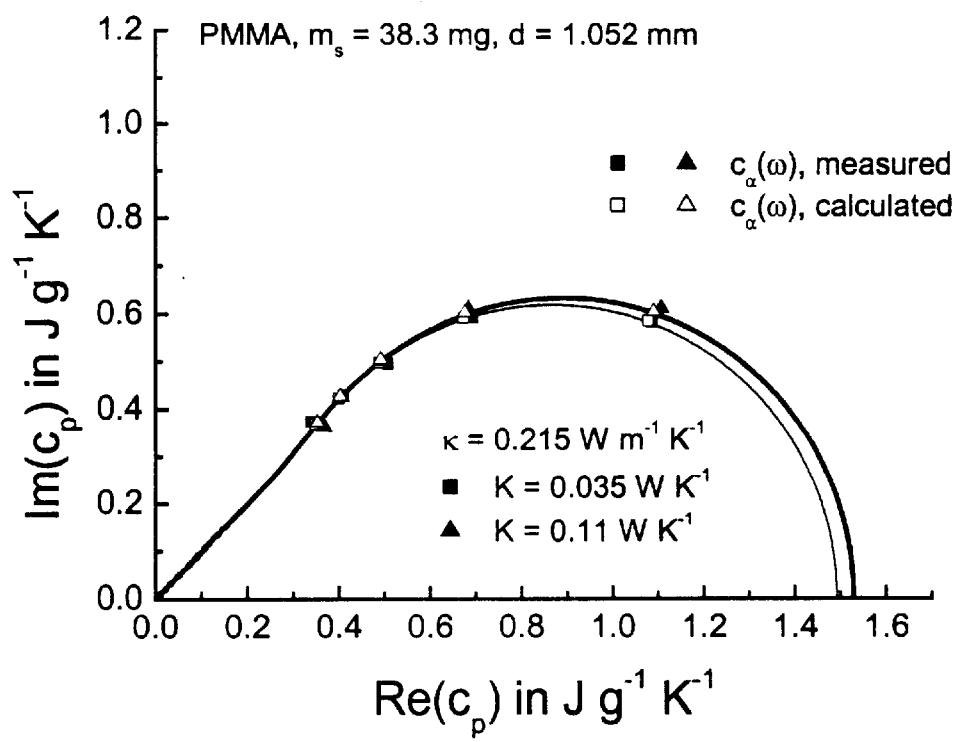

FIG. 9 shows a polar plot of $C_a(\omega_k)$, measured and calculated, for PMMA disks with thickness 0.46 mm (a) and 1.052 mm (b). The horizontal and vertical axes show the real and imaginary parts, respectively. In part (b) $C_a(\omega_k)$ values are shown for two different effective thermal contacts K=0.035 W K$^{-1}$ and K=0.11 W K$^{-1}$ and slightly different $c_p$. Two PMMA disks with different thickness give quite different values of $C_a(\omega_k)$ at the same set of frequencies. However both sets of $C_a(\omega_k)$ give almost the same value of thermal conductivity κ of about 0.214 W m$^{-1}$ K$^{-1}$ that is the property of the material. FIG. 9b shows $C_a(\omega_k)$ values are obtained from two different measurements of the same disk (d=1.052 mm, D=6.4 mm) with different amount of grease. In spite of the large difference in thermal contact ($K_1$=0.035 W K$^{-1}$, $K_2$=0.11 W K$^{-1}$) the same value for thermal conductivity (κ=0.215 W m$^{-1}$ K$^{-1}$) is obtained. It is important to mention that specific heat capacity in these two measurements (thin and thick curves) is different. Additional heat capacity of the grease in second measurement (thick curve) increases total measured heat capacity which is normalized to the same sample mass. Of course, the measured points coincide with calculated ones only to some extend. There is always some scatter in the data.

Figure 10:
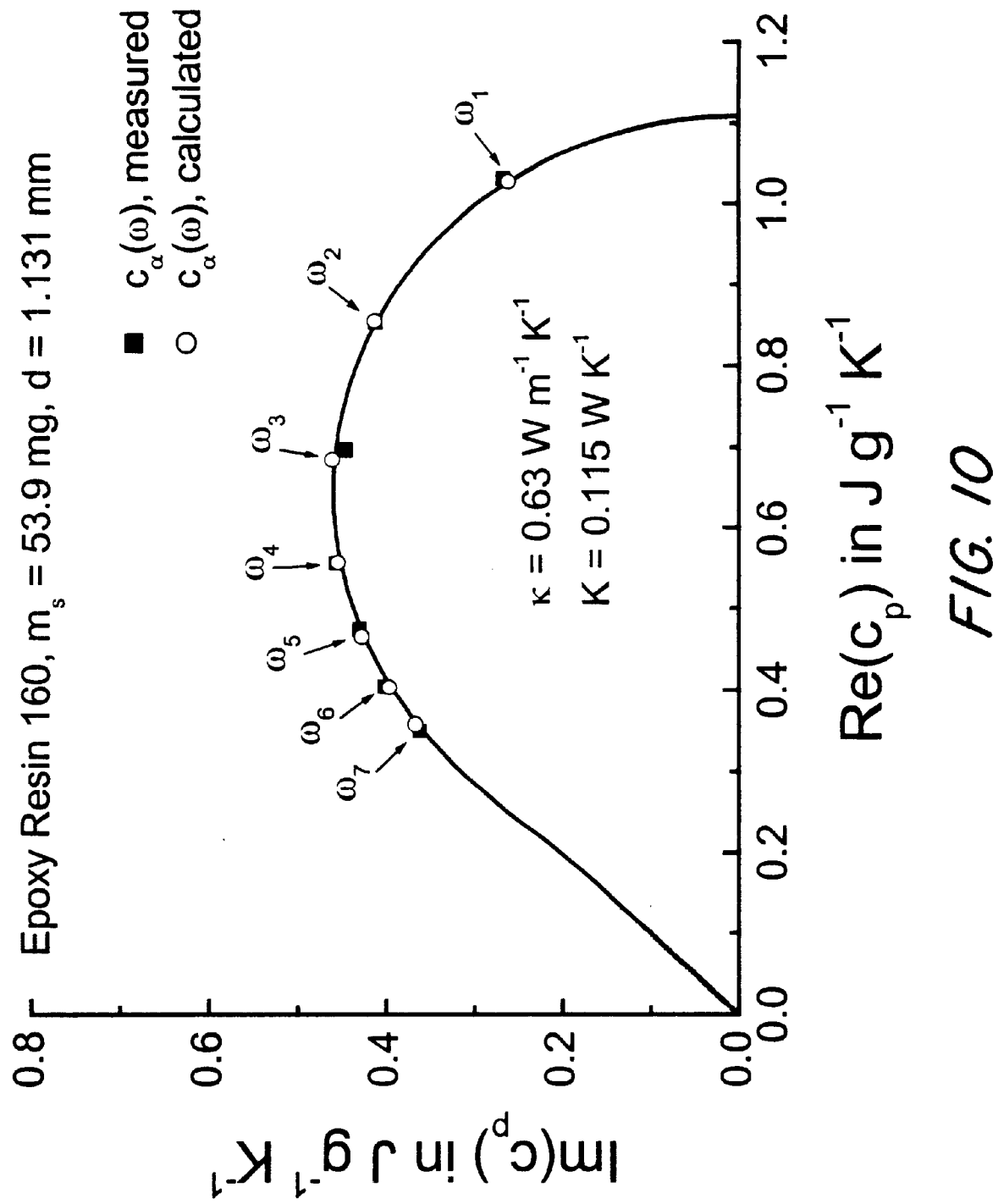
FIG. 10 shows a polar plot of $C_\alpha(\omega_k)$, measured and calculated, for Epoxy Resin 160 disk with 1.131 mm thickness. The horizontal and vertical axes show the real and imaginary parts, respectively.

FIG. 10 shows a polar plot of $C_a(\omega_k)$, measured and calculated, for Epoxy Resin 160 disk with 1.131 mm thickness. The horizontal and vertical axes show the real and imaginary parts, respectively. The results for epoxy resin 160, measured $C_a(\omega_3=3\omega_0)$ deviates relatively strong from calculated value. Some difficulties appeared when measuring material with relatively high thermal conductivity (epoxy resin 4173). At the given sample thickness, the temperature waves are damped only slightly and the finite thermal conductivity gives similar frequency dependence of $C_a(\omega)$ as the thermal contact.

Figure 11A:
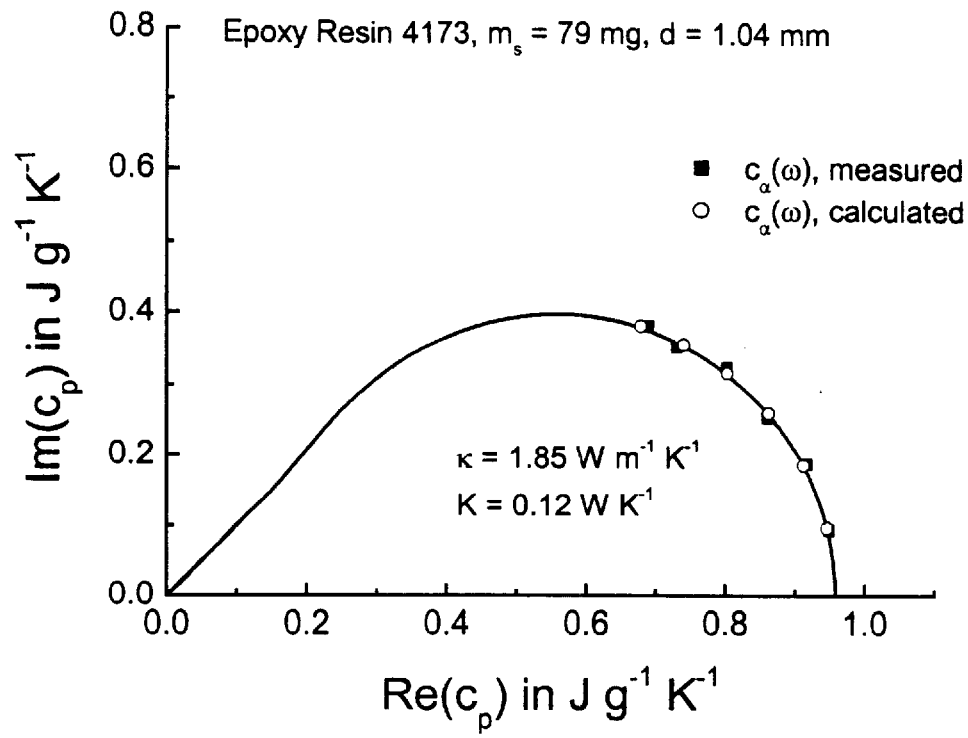
FIG. 11 shows a polar plot of $C_\alpha(\omega_k)$, measured and calculated, for Epoxy Resin 4173. The horizontal and vertical axes show the real and imaginary parts, respectively. Two different sets of parameters κ and K (κ=1.85 W m$^{-1}$ K$^{-1}$, K=0.12 W K$^{-1}$ (a) and κ=1.7 W m$^{-1}$ K$^{-1}$, K=0.13 W K$^{-1}$ (b)) describe the measured points with the same quality.
Figure 11B:
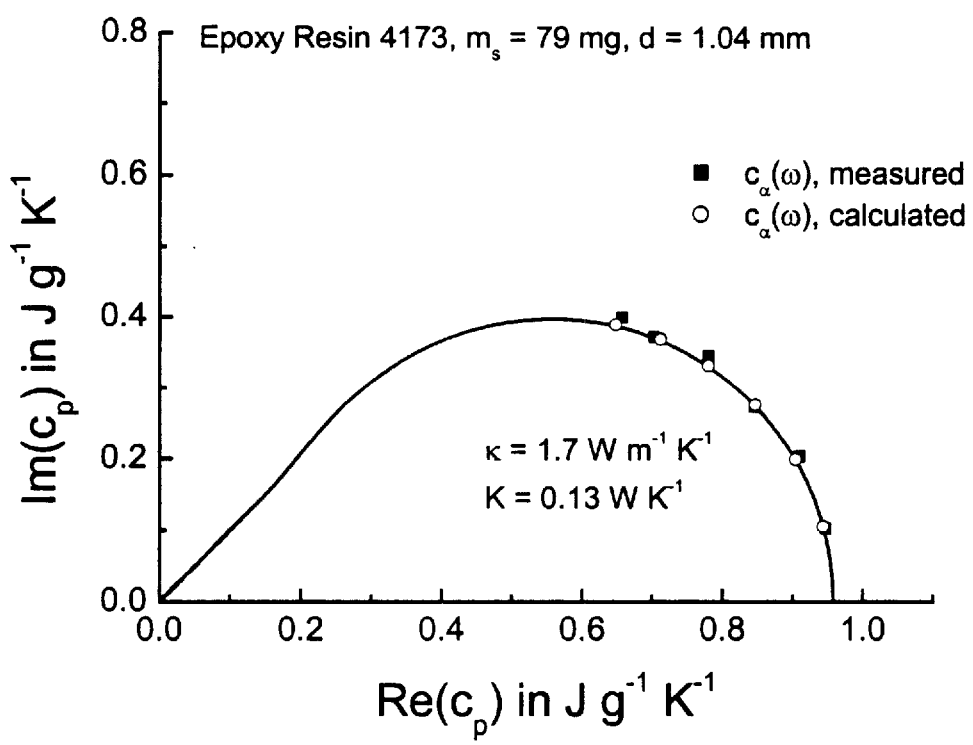

FIG. 11 shows a polar plot of $C_a(\omega_k)$, measured and calculated, for Epoxy Resin 4173. The horizontal and vertical axes show the real and imaginary parts, respectively. Two different sets of parameters κ and K (κ=1.85 W m$^{-1}$ K$^{-1}$, K=0.12 W K$^{-1}$ (a) and κ=1.7W m$^{-1}$ K$^{-1}$, K=0.13 W K$^{-1}$ (b)) describe the measured points with the same quality. Here the same measured data set can give slightly lower thermal contact K and higher thermal conductivity κ or higher K and lower κ-measured and calculated points in both cases more or less coincide. It is impossible to narrow the range of K and κ to get the correct pair. In this case the way to resolve the influences from thermal contact K and thermal conductivity κ is to increase further the frequency of temperature waves (to take much higher number for k in $\omega_k = k^* \omega_0$, which used in Eq. (1)).

Figure 12:
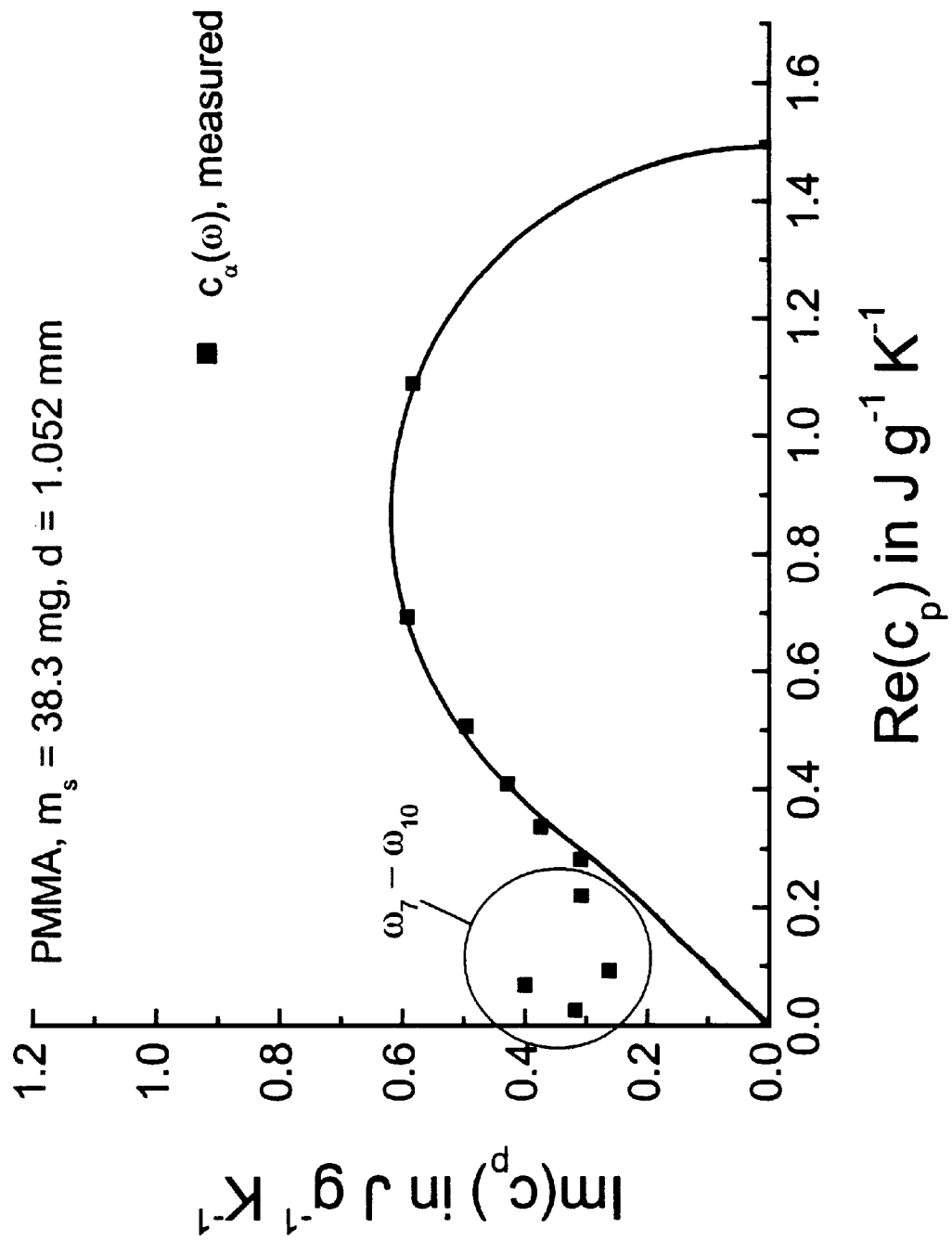
FIG. 12 shows a polar plot of $C_\alpha(\omega_k)$ for a PMMA disk. The horizontal and vertical axes show the real and imaginary parts, respectively. $C_\alpha(\omega_k)$ values, measured at high frequencies ($\omega_7$ to $\omega_{10}$), are uncertain.

FIG. 12 shows a polar plot of $C_\alpha(\omega_k)$ for a PMMA disk. The horizontal and vertical axes show the real and imaginary parts, respectively. $C_\alpha(\omega_k)$ values, measured at high frequencies ($\omega_7$ to $\omega_{10}$), are uncertain.

Figure 13A:
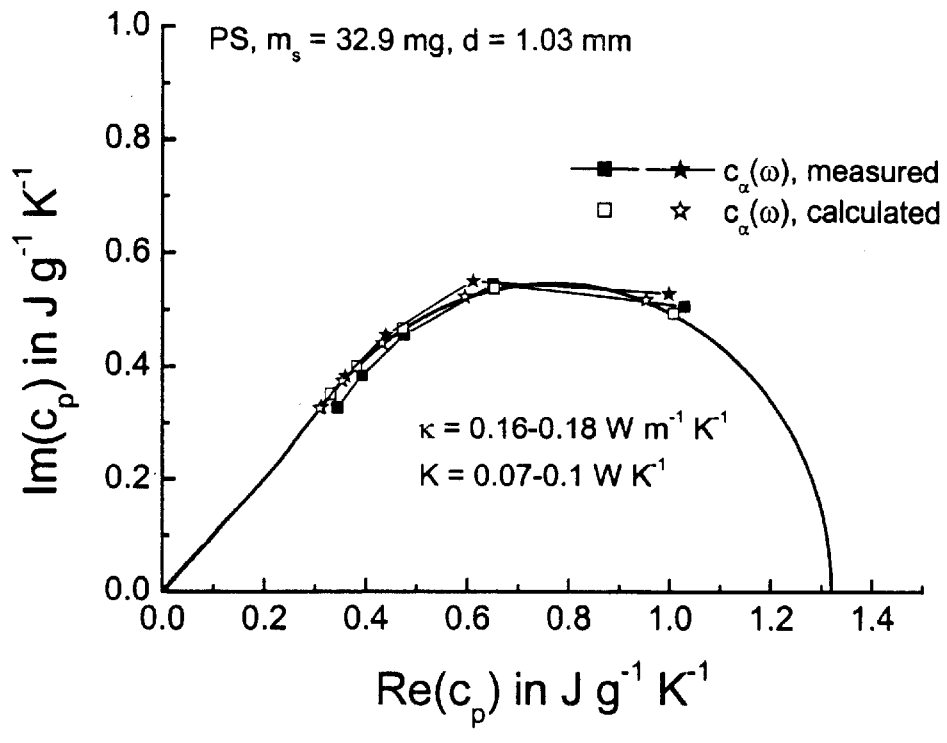
FIG. 13 shows a polar plot of $C_\alpha(\omega_k)$ for PS (a) and PMMA (b) disks. The horizontal and vertical axes show the real and imaginary parts, respectively. Measured and calculated values do not coincide simultaneously for the whole set of frequencies $\omega_k$.
Figure 13B:
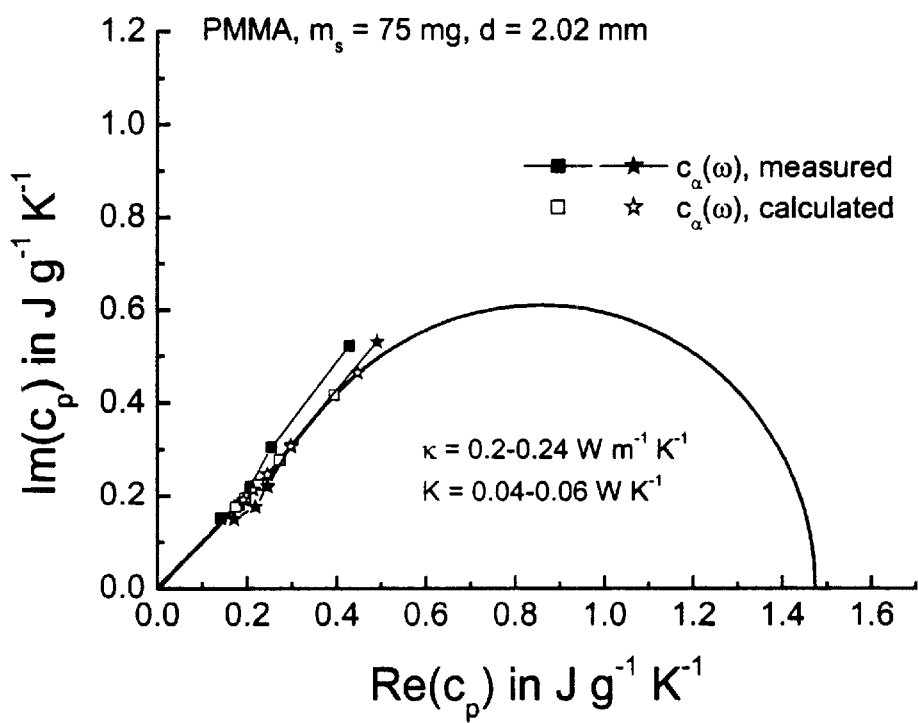

FIG. 13 shows a polar plot of $C_\alpha(\omega_k)$ for PS (a) and PMMA (b) disks. The horizontal and vertical axes show the real and imaginary parts, respectively. Measured and calculated values do not coincide simultaneously for the whole set of frequencies $\omega_k$. There could be two reasons for this disagreement: inhomogeneous thermal contact in case of thin disk, FIG. 13a, or too thick disk, FIG. 13b. In both cases the one dimensional model used for calculation could not give exact values of thermal conductivity. But one can get some range of possible value of thermal conductivity. From the width of the range one gets an impression about the validity of the model to describe the given experimental conditions, or, put another way, how faulty were the experimental conditions.

The following examples are given for the purpose of illustrating the present invention and are not intended to limit the scope in any way.

EXAMPLE 1

Polystyrene (PS) samples with know thermal conductivity were measured (ASTM interlabaratory test for thermal conductivity by modulated temperature DSC). Samples were prepared in a disc shape with a diameter D=6.4 mm and thickness d of about 0.5 and 1 mm. The measurements were performed by Perkin-Elmer Pyris-1 DSC and Lauda RC6 cooling system. DSC block temperature was set to +5° C. Purge gas was nitrogen with gas flow of 20 ml min$^{-1}$. Since the furnace floor is slightly curved and the discs are not flexible, Apiezon™ grease was utilized to get homogeneous thermal contact over the whole contact area between the bottom of the sample and the furnace. It is more important to homogenize the contact rather than to minimize its resistance. Temperature-time program shown in FIG. 8 was used to generate the spectrum of apparent heat capacity. Initial isotherm of 1 min was added to check whether heat flow drift at steady rate is remarkable. Corresponding heat flow rate after empty furnace correction is shown at FIG. 9 (since a pan was not utilized, it is necessary to subtract the heat flow measured with an empty furnace). Seven frequencies were taken into consideration such that $\omega_k = K\omega_0$, K={1, 2, ..., 7}, $\omega_0 = 2\pi/t_p$ and period $t_p = 30.75$ s. The results of thermal conductivity determination are shown in Table 1 below. FIG. 10 show two PS discs with different thickness give different values of $C_\alpha(\omega_k)$ at the same set of frequencies. Both sets of $C_\alpha(\omega_k)$ give almost the same value of thermal conductivity κ of about 0.17 W m$^{-1}$ K$^{-1}$ that is the property of the material. The measured data are also presented in polar plots, where measured apparent heat capacity $C_\alpha(\omega_k)$ (filled symbols) is compared with calculated ones (open symbols). It is possible to plot specific values for better comparison of the results for different sample masses. Solid line corresponds to theoretical curve of $C_\alpha(\omega)$, see Eq. (6).

EXAMPLE 2

Polystyrene (PMMA) samples with know thermal conductivity were measured (ASTM interlabaratory test for thermal conductivity by modulated temperature DSC). The measurements were performed by Perkin-Elmer Pyris-1 DSC and Lauda RC6 cooling system. The sample was prepared and thermal conductivity was determined the same way as in example 1. Temperature-time program shown in FIG. 8 was used to generate the spectrum of apparent heat capacity. Corresponding heat flow rate after empty furnace correction is shown at FIG. 9 (since a pan was not utilized, it is necessary to subtract the heat flow measured with an empty furnace). The results of thermal conductivity determination are shown in Table 1 below. FIG. 11 show two PMMA discs with different thickness give different values of $C_\alpha(\omega_k)$ at the same set of frequencies. Both sets of $C_\alpha(\omega_k)$ give almost the same value of thermal conductivity κ of about 0.214 W m$^{-1}$ K$^{-1}$ that is the property of the material.

EXAMPLE 3

Epoxy resins 160 (provided by Mathis Instruments) with know thermal conductivity was measured. Samples were prepared in a disc shape with a diameter D=6 mm and thickness d of about 0.5 and 1 mm. The measurements were performed by Perkin-Elmer Pyris-1 DSC and Lauda RC6 cooling system. DSC block temperature was set to +5° C. Purge gas was nitrogen with gas flow of 20 ml min$^{-1}$. Since the furnace floor is slightly curved and the discs are not flexible, Apiezon™ grease was utilized to get homogeneous thermal contact over the whole contact area between the bottom of the sample and the furnace. It is more important to homogenize the contact rather than to minimize its resistance. Temperature-time program shown in FIG. 8 was used to generate the spectrum of apparent heat capacity. Initial isotherm of 1 min was added to check whether heat flow drift at steady rate is remarkable. Corresponding heat flow rate after empty furnace correction is shown at FIG. 9 (since a pan was not utilized, it is necessary to subtract the heat flow measured with an empty furnace). Seven frequencies were taken into consideration such that $\omega_k = K\omega_0$, K={1, 2, ..., 7}, $\omega_0 = 2\pi/t_p$ and period $t_p = 30.75$ s. The results of thermal conductivity determination are shown in Table 1 below.

EXAMPLE 4

Epoxy resin 4173 (provided by Mathis Instruments) with know thermal conductivity was measured. The measurements were performed by Perkin-Elmer Pyris-1 DSC and Lauda RC6 cooling system. The sample was prepared and thermal conductivity was determined the same way as in example 3. Temperature-time program shown in FIG. 8 was used to generate the spectrum of apparent heat capacity. Corresponding heat flow rate after empty furnace correction is shown at FIG. 9 (since a pan was not utilized, it is necessary to subtract the heat flow measured with an empty furnace). The results of thermal conductivity determination are shown in Table 1 below.

TABLE 1

Comparative thermal conductivities measured at 51° C. for four different samples

| material | measured κ in W m$^{-1}$ K$^{-1}$ | expected κ in W m$^{-1}$ K$^{-1}$ |
|---|---|---|
| PS | 0.168–0.172 | 0.1562 (when taken at 47° C.) |
| PMMA | 0.212–0.215 | 0.197 (when taken at 47.2° C.) |
| epoxy resin 160 | 0.63 | 0.61 |
| epoxy resin 4173 | 1.70–1.85 | 1.83 |

What is claimed is:
1. A method of measuring the thermal conductivity of a sample comprising the steps of:
   (a) preparing a sample of the material in the form of a thin wafer having a known thickness, known dimensions, and known density;

(b) measuring the effective heat capacity of said sample;
(c) determining the apparent heat capacity by adjusting the value of said effective heat capacity of step (b);
(d) determining the specific heat capacity of said sample;
(e) determining the effective thermal contact of said sample;
(f) calculating the thermal conductivity of the material based at least upon said apparent heat capacity of said sample, said effective thermal contact of said sample, and said specific heat capacity of said sample.

2. The method of measuring the thermal conductivity of a sample of claim 1, wherein the thickness of said sample is about 1 mm or less.

3. The method of measuring the thermal conductivity of said sample of claim 1 further comprising the step of applying heat sink compound to said sample.

4. The method of measuring the thermal conductivity of a sample of claim 3, wherein said heat sink compound is grease.

5. The method of measuring the thermal conductivity of a sample of claim 1, wherein the sample is a wafer in the form of a circular disc.

6. The method of measuring the thermal conductivity of a material of claim 1, wherein said sample is a polymer.

7. The method of claim 6 wherein said polymer comprises a low thermal conducting material having a thermal conductivity value in the range of about of about 0.1 to about 2 W m$^{-1}$ K$^{-1}$.

8. The method of claim 6 wherein said polymer is selected from the group consisting of polystyrene, PMMA, epoxy resin 160, and epoxy resin 4173, and combinations of these.

9. The method of claim 1 further comprising the step of placing said sample into a sample position of a differential scanning calorimeter.

10. The method of claim 1 wherein the step of measuring the effective heat capacity of said sample using said differential scanning calorimeter further comprises the step of calculating a ratio of heat flow rate amplitude and heating rate amplitude.

11. The method of claim 10 further comprising using Laplace transformation to generate a spectrum of heat capacity.

12. The method of claim 10 further comprising using Fourier transformation to generate a spectrum of heat capacity.

13. The method of claim 10 comprising using the formulation $$C_{eff}(\omega) = \frac{A_{HF}}{A_q} = \frac{\sum_{i=1}^{n} HF_i \cos(\omega t_i) - i \sum_{i=1}^{n} HF_i \sin(\omega t_i)}{\sum_{i=1}^{n} q_i \cos(\omega t_i) - i \sum_{i=1}^{n} q_i \sin(\omega t_i)}$$

to generate a spectrum of heat capacity, wherein $C_{eff}(\omega)$ is the effective heat capacity and $A_{HF}$ is the heat flow rate amplitude and $A_q$ is the heating rate amplitude.

14. The method of claim 10 wherein temperature undergoes at least one step in temperature followed by at least one isothermal segment to generate a spectrum of heat capacity.

15. The method of claim 1 wherein the step of determining the apparent heat capacity comprises correcting for instrumental delay.

16. The method of claim 15 wherein the step of determining the apparent heat capacity further comprises applying the formulation $$C_{app}(\omega) = C_{eff}(\omega) \cdot B_2(\omega)$$

wherein Capp($\omega$) is an apparent heat capacity at frequency $\omega$, and B2($\omega$) is the dynamic calibration factor of the instrument.

17. The method of claim 1 wherein the step of determining the specific heat capacity of said sample comprises applying the formulation $$c_p = \frac{C_{eff}(0)}{m_s}$$

wherein $C_p$ is the heat capacity, $m_s$ is the sample mass, and $C_{eff}(0)$ is calculated for $\omega=0$.

18. The method of claim 1 wherein the step of determining the effective thermal contact of said sample comprises describing $C_\alpha(\omega)$ on a solid curve wherein said solid curve is a polar plot representation dependant only on the value $C_\alpha(\omega=0)$, and wherein effective thermal contact of said sample is then the value at which all $C_\alpha(\omega_k)$ points lie on the theoretical curve.

19. The method of claim 1 wherein the step of calculating the thermal conductivity of the material comprises applying the formulation $$C_a(\omega) = -\frac{1}{i\omega} \kappa \cdot S \cdot \alpha \tanh(\alpha \cdot d)$$

wherein where all measured parameters are known except thermal conductivity $\kappa$, are known wherein density $\rho$ can be calculated from the sample mass and sample size, and wherein any frequency $\omega_k \neq 0$, and wherein increasing of $\kappa$ leads to shifting the position of the $C_\alpha(\omega_k)$ point on the theoretical curve towards $C_\alpha(\omega=0)$.

20. The method of claim 1 wherein the step of calculating the thermal conductivity of a sample is determined on a computer.

21. The method of claim 1 wherein the step of calculating the thermal conductivity of a sample is realized on MS-Excel™ spreadsheet with Visual Basic™ macros.

22. A method of measuring the thermal conductivity of a sample comprising the steps of:
(a) preparing a sample of the material in the form of a thin wafer having a known thickness, known dimensions, and known density;
(b) measuring the effective heat capacity of said sample wherein heat capacity of the sample is measured with at least two different modulation frequencies to generate a heat capacity spectrum;
(c) determining the apparent heat capacity by adjusting the value of said effective heat capacity of step (b);
(d) determining the specific heat capacity of said sample;
(e) determining the effective thermal contact of said sample;
(f) calculating the thermal conductivity of the material based at least upon said apparent heat capacity of said sample, said effective thermal contact of said sample, and said specific heat capacity of said sample, wherein only one measurement for effective heat capacity of said sample was obtained.

* * * * *